(12) United States Patent
Pregel et al.

(10) Patent No.: US 7,541,466 B2
(45) Date of Patent: Jun. 2, 2009

(54) TETRAHYDROISOQUINOLINE DERIVATIVES FOR TREATING PROTEIN TRAFFICKING DISEASES

(75) Inventors: Marko J. Pregel, Arlington, MA (US); Bradford H. Hirth, Littleton, MA (US); John L. Kane, Jr., Maynard, MA (US); Shuang Qiao, San Diego, CA (US); Jill Gregory, Acton, MA (US); Lisa Cuff, Leominster, MA (US)

(73) Assignee: Genzyme Corporation, Cambridge, MA (US)

( * ) Notice: Subject to any disclaimer, the term of this patent is extended or adjusted under 35 U.S.C. 154(b) by 565 days.

(21) Appl. No.: 11/006,042

(22) Filed: Dec. 7, 2004

(65) Prior Publication Data

US 2005/0176761 A1 Aug. 11, 2005

Related U.S. Application Data

(60) Provisional application No. 60/531,873, filed on Dec. 23, 2003.

(51) Int. Cl.
*C07D 215/12* (2006.01)
(52) U.S. Cl. ..................... 546/168; 546/169; 546/153
(58) Field of Classification Search ............. 546/153, 546/168, 169; 514/311, 312, 314
See application file for complete search history.

(56) References Cited

U.S. PATENT DOCUMENTS

| 5,776,677 | A | 7/1998 | Tsui et al. | |
| 6,100,238 | A * | 8/2000 | Gyorkos et al. | 514/18 |
| 6,180,619 | B1 * | 1/2001 | Kim | 514/183 |
| 6,720,330 | B2 * | 4/2004 | Hay et al. | 514/292 |
| 6,730,777 | B1 | 5/2004 | Tsui et al. | |
| 6,902,907 | B1 | 6/2005 | Tsui et al. | |
| 6,984,487 | B1 | 1/2006 | Tsui et al. | |

FOREIGN PATENT DOCUMENTS

| WO | WO 94/04671 | | 3/1994 |
| WO | 03006014 | * | 1/2003 |

OTHER PUBLICATIONS

Su, Bioorganic & Med Chem Lett, vol. 11(22), pp. 2974-2950, 2001.*
Vendeville, Bioorg & Med Chem, vol. 10(6), pp. 1719-1729, 2002.*
Gibson, Eu J of Med Chem, vol. 37(5), pp. 379-389, 2002.*
Hyde, Biochemistry, VOl 42(21), pp. 6475-6483, 2003.*
Pedemonte, J Clin inventigation, vol. 115(9), pp. 2564-2571, 2005.*
VanGoor, Am J pyysiol Lung Cell Mol Physiol, vol. 290, pp. L1117-L1130, 2006.*
Lobell J of Biomol Screening, VOl 8(4), pp. 430-438, 2003.*
Van Goor, F., et al., "Rescue of ΔF508 CFTR Trafficking and Gating in Human Cystic Fibrosis Airway Primary Cultures by Small Molecules," *Am. J. Physiol. Lung Cell Mol. Physiol.*, doi: 10.1152/ajplung.00169.2005, pp. 1-57 (2006).
Hirth, B. H., et al., "Discovery of 1,2,3,4-tetrahydroisoquinoline-3-carboxylic acid diamides that increase CFTR mediated chloride transport," *Bioorg. Med. Chem. Lett.*, 15: 2087-2091(2005). Available online at www.sciencedirect.com.
Aridor, M. , et al., "Traffic Jam: A Compendium of Human Diseases that Affect Intracellular Transport Processes," *Traffic*, 1: 836-851 (2000).
Arispe, N., et al. "Direct Activation of Cystic Fibrosis Transmembrane Conductance Regulator Channels by 8-Cyclopentyl-1,3-dipropylxanthine (CPX) and 1,3-Diallyl-8-cyclohexylxanthine (DAX)," *J. Biol. Chem.*, 273(10): 5727-5734 (1998).
Brown, C.R., et al., "Chemical Chaperones Correct the Mutant Phenotype of the ΔF508 Cystic Fibrosis Transmembrane Conductance Regulator Protein," *Cell Stress and Chaperones*, 1(2): 117-125 (1996).
Cheng, S.H., et al., "Functional Activation of the Cystic Fibrosis Trafficking Mutant ΔF508-CFTR by Overexpression," *Am. J. Physiol.*, 268: L615-L624 (1995).
Denning, et al., "Processing of Mutant Cystic Fibrosis Transmembrane Conductance Regulator is Temperature-Sensitive," *Nature*, 358: 761-764 (1992).
Dormer, R.L., et al., "Correction of delF508-CFTR Activity with Benzo(c)quinolizinium Compounds Through Facilitation of its Processing in Cystic Fibrosis Airway Cells," *J. Cell Science*, 114: 4073-4081 (2001).
Egan, M.E., et al., "Calcium-Pump Inhibitors Induce Functional Surface Expression of ΔF508-CFTR Protein in Cystic Fibrosis Epithelial Cells," *Nature Medicine*, 8(5): 485-492 (2002).
Fischer, H., et al., "Partial Restoration of Defective Chloride Conductance in ΔF508 CF Mice by Trimethylamine Oxide," *Am. J. Physiol. Lung Cell. Mol. Physiol.*, 281: L52-L57 (2001).
Hwang, T.C., et al., "Genistein Potentiates Wild-Type and ΔF508-CFTR Channel Activity," *Am. J. Physiol.*, 273: C988-C998 (1997).
Jiang, C., et al., "Partial Restoration of cAMP-Stimulated CFTR Chloride Channel Activity in ΔF508 Cells by Deoxyspergualin," *Am. J. Physiol.*, 275: C171-C178 (1998).
Moyer, B.D., et al., "A New Frontier in Pharmacology: The Endoplasmic Reticulum as a Regulated Export Pathway in Health and Disease," *Emerging Therapeutic Targets*, 5: 165-176 (2001).
Riordan, J.R., "The Cystic Fibrosis Transmembrane Conductance Regulator," *Ann. Rev. Physiol.*, 55: 609-630 (1993).
Rosenstein, B.R., et al., "Cystic Fibrosis," *Lancet*, 351: 277-282 (1998).
Rubinstein, et al., "In Vitro Pharmacologic Restoration of CFTR-Mediated Chloride Transport with Sodium-4-Phenylbutyrate in Cystic Firbrosis Epithelial Cells Containing ΔF508-CFTR," *J. Clin. Invest.*, 100: 2457-2465 (1997).
Verkman, A.S., "Development and Biological Applications of Chloride-Sensitive Fluorescent Indicators," *Am. J. Physiol*, 259: C375-C388 (1990).

*Primary Examiner*—D. Margaret Seaman
(74) *Attorney, Agent, or Firm*—Isabelle A. S. Blundell

(57) ABSTRACT

Tetrahydroisoquinoline derivatives, pharmaceutical compositions comprising them and methods of treating disease are disclosed herein. The disclosed compounds are useful in the treatment and prevention of diseases mediated by chloride channel activity and/or protein trafficking, including, but not limited to, diseases associated with impaired mucociliary clearance such as cystic fibrosis, bronchitis, emphysema, and the like.

33 Claims, 4 Drawing Sheets

OTHER PUBLICATIONS

Welsh, M.J., et al., "Molecular Mechanisms of CFTR Chloride Channel Dysfunction in Cystic Fibrosis," *Cell*, 73: 1251-1254 (1993).

Yankaskas, et al., "Papilloma Virus Immortalized Tracheal Epithelial Cells Retain a Well-Differentiated Phenotype," *Am. J. Physiol.*, 264: C1219-C1230 (1993).

Zeitlin, P.L., et al., "Evidence of CFTR Function in Cystic Fibrosis After Systemic Administration of 4-Phenylbutyrate," *Molecular Therapy*, 6: 119-126 (2002).

Welsh, M.J., et al., Ch. 201: "Cystic Fibrosis." In *The Metabolic and Molecular Bases of Inherited Disease*, 8th Edition, online, Ed by Scriver, C.L., et al., (McGraw Hill) (2001).

* cited by examiner-

Summary of the Effects of Compound 2 on
Chloride Transport Activity in
Cells Expressing Wild-type CFTR Patch Clamp Data for CFT1 Cells
Untreated or Treated with Compound 125

Summary of Patch Clamp Data for CFT1 Cells Treated with Compound 125

Summary of Rectal Potential Difference Data
From Female Wild-Type Mice
Treated with Compound 125 or TMAO

TETRAHYDROISOQUINOLINE DERIVATIVES FOR TREATING PROTEIN TRAFFICKING DISEASES

RELATED APPLICATION

This application claims the benefit of U.S. Provisional Application No. 60/531,873, filed on Dec. 23, 2003, the entire teachings of which are incorporated herein by reference.

BACKGROUND OF THE INVENTION

Membrane proteins and secreted proteins are expressed, folded, and glycosylated in eukaryotic cells as they pass along the secretory pathway from the endoplasmic reticulum (ER) through the Golgi apparatus to the plasma membrane in a process known as protein trafficking. There are now numerous examples of genetic diseases that arise when mutations in proteins result in improper folding, including familial hypercholesterolemia, α1-antitrypsin deficiency, congenital long QT syndrome, Fabry disease, and cystic fibrosis (Moyer, B. D. and Balch, W. E., Emerging Therapeutic Targets 5 165-176 (2001)). Misfolded proteins are recognized as defective by the cell's quality control mechanisms in the ER and are degraded. Because the misfolded protein fails to traffic to the Golgi apparatus and beyond, these diseases are commonly referred to as diseases of protein trafficking or protein misfolding.

Cystic fibrosis (CF) is an example of a disease of protein misfolding. CF is the most common lethal genetic disease in Caucasians, with approximately 60,000 affected individuals in Europe and North America. Cystic fibrosis is caused by mutations in the Cystic Fibrosis Transmembrane Conductance Regulator (CFTR) protein (Riordan, J. R., Ann. Rev. Physiol. 55 609-630 (1993)). CFTR is a plasma membrane protein which belongs to the ATP-binding cassette family of membrane transport proteins. It acts as a cyclic adenosine monophosphate (cAMP)-gated chloride channel as well as a regulator of other ion transport proteins (Welsh, M. J. et al., Ch. 201 Cystic Fibrosis, in The Metabolic and Molecular Bases of Inherited Disease, 8$^{th}$ Ed. online, Ed by Scriver, C. L. et al., McGraw Hill, 2001). While hundreds of different CFTR mutations are known, almost ⅔ of CF patients are homozygous for a mutation in which phenylalanine 508 is deleted (ΔF508). ΔF508 CFTR does not fold properly in the endoplasmic reticulum, and is degraded.

CF is a disease of the epithelial tissues, including the lungs, pancreas, sweat glands, and vas deferens. CFTR is expressed in the apical membrane of epithelial cells and the ΔF508 mutation causes a loss of chloride transport function at this site. In the airways, loss of CFTR function is thought to result in changes in the quantity or 10 composition of the airway surface liquid. Consequently, mucociliary clearance is hindered and the patient is predisposed to bacterial lung infections. Mortality is the result of a progressive loss of lung function arising from the collateral damage from the immune response to chronic infections (Rosenstein, B. R. and Zeitlin, P. L., Lancet 351 277-282 (1998)).

ΔF508 CFTR is known to retain chloride channel activity, albeit at a lower level than wild-type CFTR, and a small amount of ΔF508 CFTR is able to traffic to the plasma membrane. There have been attempts to correct the ΔF508 CFTR folding defect or compensate for its effects using pharmacologic agents. Small molecules such as glycerol, dimethylsulfoxide, deuterated water, and trimethylamine-N-oxide (TMAO) are known to promote protein folding at high concentrations (Brown, C. R. et al., Cell Stress and Chaperones 1 117-125 (1996)). These so-called 'chemical chaperones' are capable of restoring some chloride channel function in cells expressing ΔF508 CFTR, and TMAO has been shown to be effective in mice, but the high concentrations required make their use as therapeutics in man impractical (Fischer, H. et al., Am. J. Physiol. 281 L52-L57 (2001)).

Compounds that increase CFTR synthesis or decrease degradation have also been evaluated. The short-chain fatty acid butyrate is thought to increase CFTR protein synthesis to a level that overwhelms the quality control apparatus and allows additional mutant CFTR to reach the plasma membrane (Cheng, S. H. et al., Am. J. Physiol. 268 L615-L624 (1995)). An analog, phenylbutyrate (PBA), is thought to assist CFTR trafficking by modulating the levels of heat shock proteins involved in the folding of CFTR and its targeting for degradation. Phenylbutyrate is an approved drug used to treat urea cycle disorders and has been evaluated in CF patients. While high doses of PBA led to detectable response in nasal potential difference measurements (Zeitlin, P. L. et al., Molecular Therapy 6 119-126 (2002)), there has so far been no convincing demonstration of a robust therapeutic effect.

Deoxyspergualin, an inhibitor of Hsp70 chaperone function, has been shown to restore ΔF508 CFTR trafficking to some extent (Jiang, C. et al., Am. J. Physiol. 275 C171-C178 (1998)), but its broad immunosuppressive effects likely preclude its use as a drug. Inhibitors of the ER calcium pump, such as thapsigargin and dibutylhydroquinone, have been shown to increase the expression of functional ΔF508 CFTR in cells and in mice, presumably by releasing mutant CFTR from calcium-dependent chaperone proteins (Egan, M. E. et al., Nature Medicine 8 485-492 (2002)). These compounds are unlikely to become drugs because altering ER calcium levels will affect the trafficking of many other proteins in addition to CFTR.

Substituted benzo[c]quinolizinium compounds have been discovered that increase chloride transport activity in cells expressing ΔF508 CFTR, including cells from a CF patient (Dormer, R. L. et al., J. Cell Science 114 4073-4081 (2001)). These compounds are active at relatively high concentrations and to date, no toxicity or pharmacokinetic data and no efficacy data in CF patients has been reported.

Another strategy has been to attempt to increase the activity of the small amount of mutant CFTR present at the plasma membrane. Genistein, a naturally occurring isoflavone, has been found to increase the open probability of the CFTR channel (Hwang, T. -C. et al., Am. J. Physiol. 273 C988-C998 (1997)). Another compound, 8-cyclopentyl-1,3-dipropylxanthine (CPX), appears to increase open probability and also assist trafficking by binding directly to CFTR (Arispe, N. et al., J. Biol. Chem. 273 5727-5734 (1998)). Both compounds are currently being evaluated in clinical trials.

To date, none of these compounds have been shown to be effective in treating cystic fibrosis. Likewise, gene therapy to introduce wild-type CFTR into epithelial cells has failed to show therapeutic efficacy thus far. Consequently, there exists an unmet medical need for compounds that restore CFTR function by assisting protein folding and trafficking. Once such compounds have been identified it is likely that they will find broader use in other diseases of protein misfolding.

SUMMARY OF THE INVENTION

It has now been found that certain substituted 1,2,3,4-tetrahydroisoquinoline derivatives are potent agents for increasing chloride ion transport and improving protein trafficking. The disclosed compounds increase chloride ion transport in cells transfected with the ΔF508 mutant CFTR gene. Many of these compounds have $EC_{50}$ values lower than 10 nM, with some as low as 3.3 nM. (See Table 2 in Example 21). Based on this discovery, these tetrahydroisoquinoline derivatives, pharmaceutical compositions comprising them and methods of improving protein trafficking and/or improving mucociliary clearance in a subject in need of such treatment are disclosed herein.

One embodiment of the present invention is a method of stimulating a protein trafficking pathway in a subject in need of protein trafficking pathway stimulation, comprising the step of administering to the subject an effective amount of a compound represented by structural formula Ia:

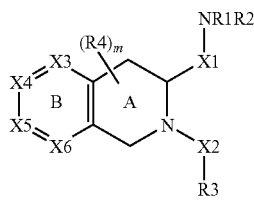

Ia or a pharmaceutically acceptable salt thereof.

Ring B is optionally substituted at any substitutable carbon. Examples of suitable substituents for Ring B are disclosed below in the section providing suitable substituents for aryl and heteroaryl groups.

X1 is —$CH_2$—, —C(O)—, —S(O)—, or —($SO_2$)—, and X2 is —$CH_2$—, —C(O)—, —C(O)$CH_2$—, —C(O)O—, —C(O)S—, —O—, —S—, or —S(O)—. In preferred embodiments, at least one of X1 and X2 is —C(O)— or —S(O)—, or more preferably, X1 and X2 are independently —C(O)— or —S(O)—. Most preferably, X1 and X2 are —C(O)—.

X3, X4, X5, and X6 are independently —N— or —CH—, wherein at least one of X3, X4, X5, and X6 is —CH—.

R1 and R2 are independently —H or an optionally substituted aliphatic, aryl, heteroaryl, heterocyclic, cycloalkyl, peptide, or amino acid group, provided that R1 and R2 are not both —H. Alternatively, R1 and R2, taken together with the nitrogen to which they are bonded, are an optionally substituted heterocyclic group. Preferred substituents for R1 and R2 include halogen, C1-C4 alkyl, C1-C4 aminoalkyl, C1-C4 alkoxy, aryl, aminoaryl, heteroaryl, nonaromatic heterocycle, or C3-C7 cycloalkyl.

R3 is an optionally substituted aryl, heteroaryl, cycloalkyl, or heterocyclic group.

The variable m is 0, 1 or 2.

Each R4 is independently halogen, —OH, —SH, —$R^a$, —$OR^a$, —$SR^a$, —$NH_2$, $NHR^a$, —$NR^a_2$, —C(O)$NR^a_2$, —$CF_3$, —CN, or —$NO_2$, wherein each $R^a$ is independently a C1-C5 branched or linear alkyl group.

Another embodiment of the method is administering the compound represented by structural formula Ia to improve mucociliary clearance in a subject in need of improved mucociliary clearance.

Another embodiment of the invention is a compound represented by structural formula Ib.

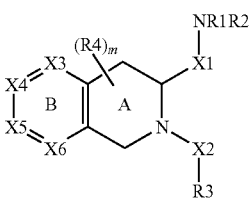

Ib

X1 and X2 are independently —C(O)— or —S(O)—. Preferably, X1 and X2 are —C(O)—.

X3, X4, X5, and X6 are independently —N— or —CH—, wherein at least one of X3, X4, X5, and X6 is —CH—.

Ring B is optionally substituted at any substitutable carbon. Examples of suitable substituents for Ring B are disclosed in the section below providing suitable substituents for aryl and heteroaryl groups.

The variable m is 0, 1 or 2.

Each R4 is independently halogen, —OH, —SH, —$R^a$, —$OR^a$, —$SR^a$, —$NH_2$, $NHR^a$, —$NR^a_2$, —C(O)$NR^a_2$, —$CF_3$, —CN, or —$NO_2$, wherein each $R^a$ is independently a C1-C5 branched or linear alkyl group.

In structural formula Ib, in one alternative (i), R3 is a six-membered aryl or heteroaryl group that is substituted or is fused to another ring. R1 and R2, taken together with the nitrogen to which they are bonded, are an optionally substituted 6-membered heterocyclic group, or R1 is —H and R2 is —X7-R6. X7 is a covalent bond, a C5-C12 linear or branched aliphatic group containing 1, 2, or 3 double bonds, or a C1-C12 alkyl chain optionally interrupted by —O— or —S—. R6 is —SH, diphenylmethylene, or a 5 or 6 membered aryl, heteroaryl, heterocyclic or monocyclic C4-C6 cycloalkyl group. Each cyclic group represented by R6 is optionally substituted with one or more groups selected from C4-C6 cycloalkyl, halogen, —$CF_3$, —$R^d$, —$OR^d$, —$SR^d$, —$COR^d$, —OH, —SH, phenyl, phenoxyl, benzyl, benzoyl, N-morpholinyl, —$NR^d_2$, —$NR^d COR^e$, N-aniline, —$NO_2$, and —CN. Each $R^d$ and $R^e$ is independently a C1-C7 branched or linear alkyl group.

In structural formula Ib, in another alternative (ii), R3 is an optionally substituted 2-naphthyl, 6-(1,4 benzodioxan)yl, 6-indolyl, or 2-(9-fluorenon)yl group, or a phenyl or pyridyl group substituted with one or more groups selected from halogen, —$CF_3$, —$NO_2$, —CN, —$R^c$, —$OR^c$, and —$XR^f$. X is —O—, —S—, —C(O)—, —S(O)—, —$CH_2$—, —$CH_2CH_2$—, —$OCH_2$—, —$OCH_2CH_2$—, —$SCH_2$—, or —$SCH_2CH_2$—. $R^f$ is an optionally substituted phenyl, pyridyl, N-pyridyl, A-morpholinyl, furanyl, thienyl, isoxazolyl, imidazolyl, pyrazolyl, pyrrolyl, pyrrolidyl, piperidyl, piperazyl, benzofuranyl, tetrazolyl, thiazolyl, tetrazolyl, benzothiazolyl, benzimidazolyl cyclobutyl, cyclopentyl, or cyclohexyl group. R1 and R2, taken together with the nitrogen to which they are bonded, are an optionally substituted heterocyclic group; or, R1 and R2 are independently —H or an optionally substituted aliphatic, aryl, heteroaryl, heterocyclic, or monocyclic cycloalkyl group, provided that R1 and R2 are not both —H. Each $R^c$ is independently a C1-C5 branched or linear alkyl group.

The disclosed compounds are expected to be useful in the treatment and prevention of diseases mediated by epithelial chloride transport activity and/or protein trafficking, including, but not limited to, diseases associated with impaired mucociliary clearance such as CF, bronchitis, emphysema, and the like. Also included are diseases related to protein trafficking, such as CF, $\alpha_1$-antitrypsin deficiency, hereditary hematochromatosis, protein C deficiency, nephrogenic diabetes insipidus, familial hypercholesterolemia, hyperphenylalaninemia, Type I oculocutaneous albinism, persistent hyperinsulemic hypoglycemia of infancy, Tay-Sachs Disease, Parkinson's disease, Alzheimer's disease, chronic obstructive pulmonary disease, asthma, bronchitis, and prion diseases.

DETAILED DESCRIPTION OF THE INVENTION

Figure 1:
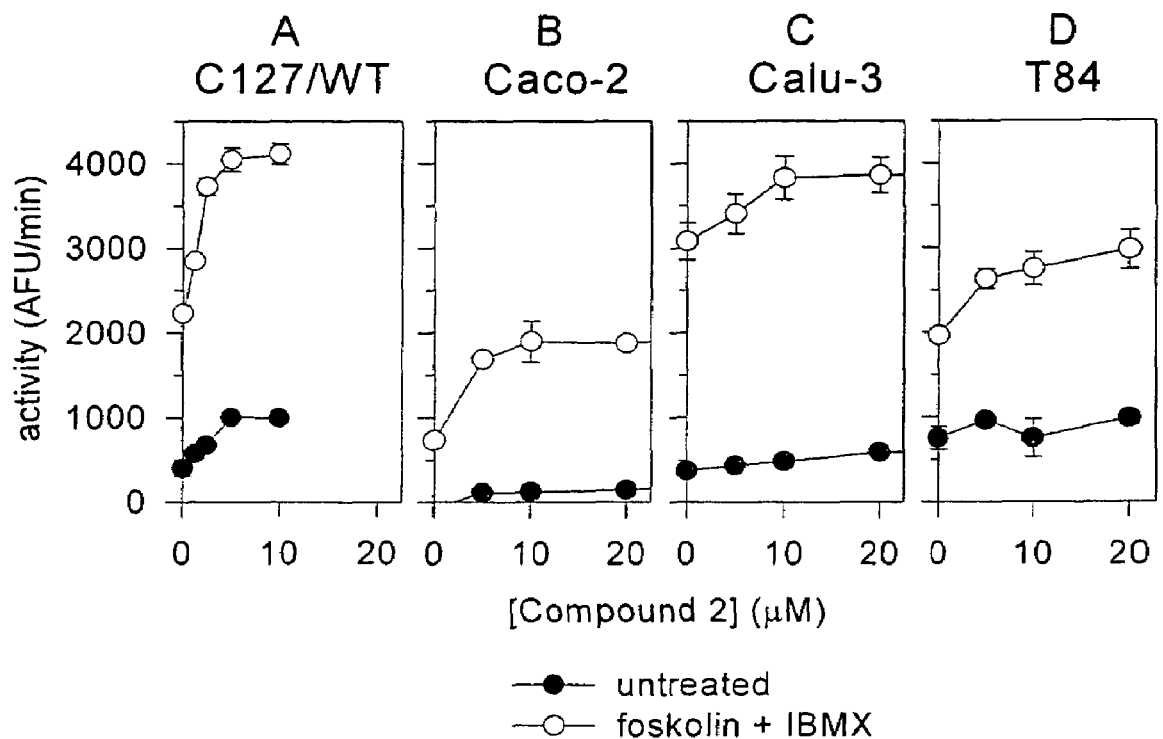
FIG. 1 is a series of graphs A-D showing that Compound 2 increases cAMP (cyclic adenosine monophosphate)-dependent chloride transport activity in four different human cell lines expressing wild-type CFTR. Chloride transport activity is tested using the fluorescent chloride-sensitive dye M4QAE (N-(ethoxycarbonylmethyl)-6-methoxy quinolinium bromide) in cells treated with increasing concentrations of Compound 2, expressed in μM, in the presence (open circles) and absence (filled circles) of the cAMP agonist forskolin.

Disclosed herein is a method of and compounds for treating diseases associated with protein trafficking and/or chloride ion transport in a subject. The method is particularly effective in improving chloride ion transport associated with CFTR, which is expected to lead to, for example, improved mucociliary clearance in a subject with cystic fibrosis (CF).

The term "aryl" group, (e.g., the aryl groups represented by R1-R3, or R6) refers to carbocyclic aryl groups such as phenyl, naphthyl, and anthracyl. The term "aryl" can also refer to aryl rings fused to other rings, e.g., cycloalkyl rings, non-aromatic heterocyclic rings, and the like. For example, aryl can include 1,4-benzodioxanyl, 1,3-benzodioxoyl, fluorenyl, fluorenonyl, and the like.

The term "heteroaryl" group (e.g., the heteroaryl groups represented by R1-R3, or R1 and R2 taken together) refers to aromatic groups containing at least one heteroatom, e.g., N, O or S, in the ring. For example, heteroaryl groups can include imidazolyl, isoimidazolyl, thienyl, furanyl, pyridyl, pyrimidyl, pyranyl, pyrazolyl, pyrrolyl, pyrazinyl, thiazolyl, isothiazolyl, oxazolyl, isooxazolyl, 1,2,3-triazolyl, 1,2,4-triazolyl, tetrazolyl, and the like.

"Heteroaryl" groups also include fused polycyclic ring systems in which the parent heteroaryl ring is fused to one or more aryl, cycloalkyl, heteroaryl, or heterocyclic rings. Examples include benzothienyl, benzofuranyl, indolyl, isoindolyl, quinolinyl, isoquinolinyl, quinoxalinyl, quinazolinyl, benzothiazolyl, benzoisothiazolyl, benzooxazolyl, benzoisooxazolyl, benzimidazolyl, benzoxanyl, benzopyrrolidinyl, benzopiperidinyl, benzoxolanyl, benzothiolanyl, benzothienyl, 1,8-benzodiazinyl, 3-1H-benzimidazol-2-onyl, indanyl, carbazolyl, acridinyl, phenanthrolinyl, phenazinyl, naphthyridinyl, phthalazinyl, cinnolinyl, thianthracyl, chromanyl, chromenyl, and tetrahydronaphthyl.

Rings that are fused share two adjacent ring atoms, for example, naphthalene consists of two fused phenyl rings that share two adjacent ring atoms. A ring that is fused to another ring, for example, R3, can be a naphthyl, quinolinyl, anthracyl, fluorenyl, benzimidazolyl, 1,4-benzodioxanyl, 1,3-benzodioxolyl, benzothienyl, benzofuranyl, chromanyl, chromenyl, tetrahydronaphthyl, and the like.

The term "ring" means any cyclic group, e.g., aryl, heteroaryl, cycloalkyl, and the like. As used herein, a "monocyclic" ring is a group that is not fused to another ring, but can include a ring that is substituted with another ring. For example, the pyridine and phenyl rings in 2-phenyl pyridine are both monocyclic while naphthalene is polycyclic.

The term "heterocyclic" and "non-aromatic heterocyclic" (e.g., the heterocyclic groups represented by R1-R3 or a cyclic group represented by —NR1R2, wherein R1 and R2 are taken together with the nitrogen to which they are bonded to form a ring) refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, and 1-phthalimidinyl.

Each of the disclosed compounds contains at least one chiral center. For example, the carbon at the 3-position of the central tetrahydroisoquinoline moiety, where X1 is attached in structural formula I, is a chiral center in each disclosed compound. The presence of chiral centers in a molecule gives rise to stereoisomers. For example, a pair of optical isomers, referred to as "enantiomers", exist for every chiral center in a molecule, and a pair of diastereomers exist for every chiral center in a compound having two or more chiral centers. Where a structural formula represents a compound with one or more chiral centers and does not explicitly depict stereochemistry, it is to be understood that the formula encompasses enantiomers free from the corresponding optical isomer, racemic mixtures, and mixtures enriched in one enantiomer relative to its corresponding optical isomer. Where a structural formula represents a compound with two or more chiral centers and the structural formula does not explicitly depict stereochemistry, it is to be understood that the formula represents every diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s), and mixtures of diastereomeric pairs in which one diastereomeric pair is enriched relative to the other diastereomeric pair(s).

The term "alkyl" (e.g., the alkyl groups represented by R1, R2, and R3), used alone or as part of a larger moiety (e.g., aralkyl, alkoxy, alkylamino, alkylaminocarbonyl, haloalkyl), is a straight or branched non-aromatic hydrocarbon which is completely saturated but for the valence bond linking it to the remainder of the structure, e.g., monovalence for a terminal methyl group, divalence for a methylene group, and trivalence for a methine group. Typically, a straight or branched alkyl group has from 1 to about 10 carbon atoms. preferably from I to about 4 carbon atoms. Examples of suitable straight or branched alkyl group include methyl, ethyl, n-propyl, 2-propyl, n-butyl, sec-butyl, tert-butyl, pentyl, hexyl, heptyl, octyl, nonyl, decyl, and the like. A C1-C10 straight or branched alkyl group or a C3-C8 cyclic alkyl group are also referred to as a "lower alkyl" group. An "alkoxy" group refers to an alkyl group that is connected through an intervening oxygen atom, e.g., methoxy, ethoxy, 2-propyloxy, tert-butoxy, 2-butyloxy, 3-pentyloxy, and the like.

An aliphatic group is an alkyl group that optionally contains one or more units of unsaturation, i.e., carbon-carbon double or triple bonds. A cycloaliphatic group is a cyclic aliphatic group, provided that a cycloaliphatic group is not aromatic.

The term "cycloalkyl group" (e.g., the cycloalkyl groups represented by R1, R2, and R3) is a cyclic alkyl group has from 3 to about 10 carbon atoms, preferably from 3 to about 8. Examples of suitable cycloalkyl groups include cyclopropyl, cyclobutyl, cyclopentyl, cyclohexyl, cycloheptyl and cyclooctyl. A "cycloalkoxy" group refers to a cycloalkyl group that is connected through an intervening oxygen atom, e.g., cyclopentyloxy, cyclohexyloxy, and the like.

Suitable substituents on alkyl, cycloalkyl, aryl, and heteroaryl groups, and the like, (e.g., those represented by R1-R5, Rings A and B, and the like) are those that do not substantially interfere with the pharmaceutical activity of the disclosed compound. A compound or group can have one or more substituents, which can be identical or different. Examples of suitable substituents for a substitutable carbon atom in an alkyl, cycloalkyl, heterocyclic, aryl (e.g., suitable substituents for Ring B), or heteroaryl group include —OH, halogen (—Br, —Cl, —I and —F), —R, —OR, —CH$_2$R, —CH$_2$CH$_2$R, —OCH$_2$R, —CH$_2$OR, —CH$_2$CH$_2$OR, —CH$_2$OC(O)R, —O—COR, —COR, —SR, —SCH$_2$R, —CH$_2$SR, —SOR, —SO$_2$R, —CN, —NO$_2$, —COOH, —SO$_3$H, —NH$_2$, —NHR, —N(R)$_2$, —COOR, —CHO, —CONH$_2$, —CONHR, —CON(R)$_2$, —NHCOR, —NR-COR, —NHCONH$_2$, —NHCONHR, —NHCON(R)$_2$, —NRCONH$_2$, —NRCONRH, —NTRCON(R)$_2$, —C(=NH)—NH$_2$, —C(=NH)—NHR, —C(=NH)—N(R)$_2$, —C(=NR)—NH$_2$, —C(=NR)—NHR, —C(=NR)—N(R)$_2$, —NH—C(=NH)—NH$_2$, —NH—C(=NH)—NHR, —NH—C(=NH)—N(R)$_2$, —NH—C(=NR)—NH$_2$, —NH—C(=NR)—NHR, —NH—C(=NR)—N(R)$_2$, —NRH—C(=NH)—NH$_2$, —NR—C(=NH)—NHR, —NR—C(=NH)—N(R)$_2$, —NR—C(=NR)—NH$_2$, —NR—C(=NR)—NHR, —NR—C(=NR)—N(R)$_2$, —SO$_2$NH$_2$, —SO2NHR, —SO$_2$NR$_2$, —SH, —SO$_k$R (k is 0, 1 or 2) and —NH—C(=NH)—NH$_2$. Each R is independently an alkyl, cycloalkyl, benzyl, aryl, or heteroaryl group that is optionally substituted in a like manner. Preferably, R is unsubstituted. In addition, —N(R)$_2$, taken together, can also form a substituted or unsubstituted heterocyclic group, such as pyrrolidinyl, piperidinyl, morpholinyl and thiomorpholinyl. Examples of substituents on group represented by R include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

Ring B in structural formulas Ia and Ib, and in structural formulas II-V below, is optionally substituted as described in the preceding paragraph. Preferably, Ring B is substituted at any substitutable carbon with zero, one, or more groups R5.

Each R5 can be independently selected from —OH, halogen, —R, —OR, —SR, —CH$_2$R, —CH$_2$CH$_2$R, —OCH$_2$R, —CH$_2$OR, —CH$_2$CH$_2$OR, —CH$_2$OC(O)R, —O—COR, —COR, —SR, —SCH$_2$R, —CH$_2$SR, —SOR, —SO$_2$R, —CN, —NO$_2$, —COOH, —SO$_3$H, —NH$_2$, —NHR, —N(R)$_2$, —COOR, —CHO, —CONH$_2$, —CONHR, —CON(R)$_2$, —NHCOR, —NRCOR, —NHCONH$_2$, —NHCONRH, —NHCON(R)$_2$, —NRCONH$_2$, —NRCONRH, —NRCON(R)$_2$, —SO$_2$NH$_2$, —SO$_2$NHR, —SO$_2$NR$_2$, —SH, —SO$_k$R (k is 0, 1 or 2), or —SR, wherein each R is as defined in the preceding paragraph. More preferably, each R5 is independently selected from halogen, —OH, —SH, R$^b$, —OR$^b$, —SR$^b$, —NH$_2$, —NHR$^b$, —NR$^b{}_2$, —C(O)NR$^b{}_2$, —CF$_3$, —CN, and —NO$_2$, wherein each R$^b$ is independently a C1-C5 branched or linear alkyl group. Alternatively, R5 is halogen, —OH, —R$^b$, —OR$^b$, —NH$_2$, —NHR$^b$, —NR$^b{}_2$, —C(O)NR$^b{}_2$, —CF$_3$, —CN, or —NO$_2$. More preferably, R5 is halogen, —OH, —CH$_3$, —OCH$_3$, or —NH$_2$. Most preferably, Ring B is unsubstituted.

Suitable substituents on the nitrogen of a heterocyclic group or heteroaryl group include —R', —N(R')$_2$, —C(O)R', —CO$_2$R, —C(O)C(O)R', —C(O)CH$_2$ C(O)R', —SO$_2$R', —SO$_2$N(R')$_2$, —C(=S)N(R')$_2$, —C(=NH)—N(R')$_2$, and —NR'SO$_2$R'. R' is hydrogen, an alkyl, alkoxy, cycloalkyl, cycloalkoxy, phenyl, phenoxy, benzyl, benzyloxy, heteroaryl, or heterocyclic group that is optionally substituted. Examples of substituents on the groups represented by R' include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. Preferably, R' is unsubstituted.

"Protein trafficking" is the process by which membrane proteins and secreted proteins are expressed, folded, and glycosylated in eukaryotic cells as they pass along the secretory pathway from the endoplasmic reticulum (ER) through the Golgi apparatus to the plasma membrane. Protein trafficking diseases include CF, wherein mutations in the CFTR gene lead to retention of CFTR by the endoplasmic reticulum, where the CFTR is prematurely degraded. Because the disclosed compounds prevent retention or degradation, they can be used in the treatment of the most common CF mutation, known as ΔF508, and possibly also for other trafficking-defective CF mutations, such as N1303K, ΔI507, and the like. See Welsh, M J; Smith, A E. *Cell* 1993, 73, 1251-1254, the entire teachings of which are incorporated herein by reference.

Other protein trafficking diseases that can be treated with the disclosed invention include α$_1$-antitrypsin deficiency, hereditary hematochromatosis, protein C deficiency, nephrogenic diabetes insipidus, familial bypercholesterolemia, hyperphenylalaninemia, Type I oculocutaneous albinism, persistent hyperinsulemic hypoglycemia of infancy, Tay-Sachs Disease, Parkinson's disease, Alzheimer's disease, chronic obstructive pulmonary disease, asthma, and prion diseases. Also, a subject can be treated by improving a normal trafficking pathway. For example, in normal, non-CF subjects, i.e., expressing wild type CFTR, trafficking leads to degradation of up to 70% of the CFTR that is synthesized. Thus, normal subjects can be treated for conditions involving impaired mucociliary clearance, include emphysema, bronchitis, bacterial, fungal, viral, or parasitic infections, and the like (Aridor, M; Hannan, L A. *Traffic* 2000, 1, 836-851, the entire teachings of which are incorporated herein by reference) since increasing the level of wild-type CFTR can increase the height of the airway surface liquid layer, facilitating the transport of mucus.

"Mucociliary clearance" is the process by which cells produce and clear mucus. For example, cells in the lungs produce mucus, which traps inhaled contaminants such as particles, pollutants, pathogens, and the like. Small hairs, or cilia, continuously move the mucus out of the lungs to remove these entrapped contaminants. The cilia depend on the characteristics of mucus and associated fluids at the mucociliary interface to function.

Increasing chloride ion transport, for example, by administering the disclosed compounds, can change the intracellular and extracellular aqueous ion concentrations, in particular, chloride ion and sodium ion, which can change the height and/or composition of the airway surface liquid. These changes affect the properties of the mucus and associated fluids, and can lead to improved mucociliary clearance. For example, increased chloride ion transport across a cell membrane can lead to increased ion and/or water transport, whereby the height of the airway surface liquid can be increased, allowing the cilia to more effectively clear the mucus which overlays both the airway surface liquid and cilia.

"Improving mucociliary clearance" means an increase in the rate of mucus transport in the airways that is associated with patient benefit. For example, improved mucociliary clearance in a subject suffering from CF can lead to clinical benefits such as a change in the composition of mucus and associated fluids, leading to easier expulsion of mucus from the lungs. This can lead to reduction in chronic lung infections, improvement in lung capacity, recovery from chronic infections, and the like. "Improving mucociliary clearance" also refers to mucus transport associated with other tissues, including nasal, oral, conjunctival, esophageal, gastric, pancreatic, gall bladder, intestinal, colorectal, and the like. Also included is mucus transport in reproductive tissues including vaginal, urethral, vas deferens, ovarian, fallopian, testicular, and the like.

"Stimulating a protein trafficking pathway" means increasing the overall flux of a target protein through the secretory pathway. The increase in overall flux can be due to an increased amount of target protein, or increased activity of individual protein molecules, e.g., chaperone molecules, and the like. This can occur by a number of mechanisms, for example, a folding step could be enhanced, a degradation process could be inhibited, a protein delivery process could be enhanced, a combination of the preceding, and the like. A subject that is in need of such stimulation has symptoms that can be alleviated when a protein trafficking pathway is stimulated, for example, a ΔF508 CF subject, where increasing protein trafficking can improve mucociliary clearance. A subject with wild type CFTR can also be treated to improve mucociliary clearance. For example, CFTR trafficking can be stimulated to improve mucociliary clearance in subjects that have a bacterial, fungal, viral, or parasitic lung infection, or that have an acquired condition from pollutant exposure, such as emphysema, or that have a response to industrial chemicals or pollutants, such as coal dust, and the like.

A "subject" includes mammals, e.g., humans, companion animals (e.g., dogs, cats, and the like), farm animals (e.g., cows, sheep, pigs, horses, and the like) and laboratory animals (e.g., rats, mice, guinea pigs, and the like). In a preferred embodiment of the disclosed method, the subject is human. A subject in need of treatment is suffering from a disease or condition, the symptoms of which may be alleviated by stimulating a protein trafficking pathway or by increasing chloride ion transport. Typically, a subject will be treated for a disease that is caused, at least in part, by a protein trafficking defect. Alternatively, the method is used to improve mucociliary clearance in a subject in need of improved mucociliary clearance. Preferably, the method is used to treat a subject that has cystic fibrosis.

An "effective amount" of a compound of the disclosed invention is the quantity which, when administered to a subject in need of treatment, improves the prognosis of the subject, e.g., delays the onset of and/or reduces the severity of one or more of the subject's symptoms. The amount of the disclosed compound to be administered to a subject will depend on the particular disease, the mode of administration, and the characteristics of the subject, such as general health, other diseases, age, sex, genotype, body weight and tolerance to drugs. The skilled artisan will be able to determine appropriate dosages depending on these and other factors. Effective amounts of the disclosed compounds typically range between about 0.01 mg/kg per day and about 100 mg/kg per day, and preferably between 0.1 mg/kg per day and about 10 mg/kg/day.

Preferably disclosed compounds or pharmaceutical formulations containing these compounds are in unit dosage form for administration to a subject. The unit dosage form can be any unit dosage form known in the art including, for example, a capsule, an I.V. bag, a tablet, a single pump on an aerosol inhaler, or a vial. The quantity of active ingredient (i.e., a compound of structural formula I or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, pulmonary, rectal, transdermal, subcutaneous, intravenous, intramuscular, intraperitoneal and intranasal.

The term "pulmonary" as used herein refers to any part, tissue or organ whose primary function is gas exchange with the external environment, i.e., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli, and the like). For purposes of the present invention, "pulmonary" is also meant to include a tissue or cavity that is contingent to the respiratory tract, in particular, the sinuses.

A "pharmaceutically acceptable salt" of the disclosed compound can be used in the disclosed methods. For example, an acid salt of a compound containing an amine or other basic group can be obtained by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine.

The compounds described herein, and thepharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, $19_{th}$ edition, Mack Publishing Co., Easton, Pa. (1995).

For oral administration, the disclosed compounds or salts thereof can be combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like.

For parenteral administration of the disclosed compounds, or salts thereof, can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition to the formulations described previously, the compounds may also be formulated as a depot preparation. Suitable formulations of this type include biocompatible and biodegradable polymeric hydrogel formulations using crosslinked or water insoluble formulations of polysaccharides, polyethylene oxides, polyacrylates, and the like. Such long acting formulations may be administered by implantation, for example, subcutaneously or intramuscularly or by intramuscular injection. Preferably, they are implanted in the microenvironment of an affected organ or tissue. Thus, for example, the compounds may be formulated with suitable polymeric or hydrophobic materials, for example, as an emulsion in an acceptable oil, or ion exchange resins, or as sparingly soluble derivatives, for example, as a sparingly soluble salt.

In addition to the formulations described previously, the compounds may also be formulated as a topical preparation. Suitable formulations of this type include biocompatible oil, wax, gel, powder, polymer, or other liquid or solid carriers. Such formulations may be administered by applying directly to affected tissues, for example, a liquid formulation to improve clearance of mucus secreted by conjunctival tissue can be administered dropwise to the subject's eye.

In addition to the formulations described above, a formulation can optionally include one or more additional drugs, e.g., antibiotics, anti-microbials, anti-fungals, anti-virals, antihelminthics, anti-inflammatories, steroids, decongestants, bronchodialators, and the like. Examples of co-therapies for infections or complications due to CF include tobramycin and other aminoglycosides, ciprofloxacin and other fluoroquinolones, rifabutin, ethambutol, clarithromycin, clofazimine, aztreonam, cephalothin, cefazolin, nafcillin, ticarcilin, clavulanate, gentamicin, amikacin, ceftazidime, piperacillin, imipenem, cefepime, chloramphenicol, colistin, dicloxacillin, cefaclor, amoxicillin, azithromycin, trimethoprim /sulfa, cefpodoxime, tetracyclines, amiloride and meropenem. Also, an anti-inflammatory drug or steroid can be used such as ibuprofen, prednisone (corticosteroid) or pentoxifylline. Another suitable co-therapy is administering dornase alfa (DNase), nacystelyn, gelsolin or hypertonic saline, which reduce mucus buildup, or administering a decongestant or bronchodilator (e.g, a beta adrenergic receptor agonist, an anticholinergic drug, theophylline, and the like).

In addition to the formulations described previously, the compounds may also be formulated to deliver the active agent by pulmonary means, e.g., administration of an aerosol formulation containing the active agent from, for example, a manual pump spray, nebulizer or pressurized metered-dose inhaler. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

When administering the drug, the patient can actuate the drug delivery device. The actuation releases a fraction of the formulation from within the canister to the external environment. A force, created by vaporized propellant, expels the drug into the air and away from the device. The patient then inhales the aerosolized drug. The metering valve controls the amount of the formulation released, which, in turn, effectively controls the amount of drug available for inhalation by the patient.

Particles for pulmonary administration are typically substantially non-acicular morphology, i.e, more rounded than needle-like. The particles will preferably have an average particle size in the range of about 0.5 micrometer to about 10 micrometer, more preferably in the range of about 1 micrometer to about 7.5 micrometer, and most preferably in the range of about 1 micrometer to about 5 micrometer. Preferably, greater than about 85%, more preferably greater than about 95%, and most preferably greater than about 98% of the population of particles in the formulation will fall within the desired particle size range, e.g., about 0.5 micrometer to about 10 micrometer, about 1 micrometer to about 7.5 micrometer, and so on.

To ensure that the drug particles for pulmonary administration have the proper size and shape, the particles may be analyzed using known techniques for determining particle morphology. For example, the particles can be visually inspected under a microscope and/or passed through a mesh screen. Preferred techniques for visualization of particles include scanning electron microscopy (SEM) and transmission electron microscopy (TEM). Particle size analysis may take place using laser diffraction methods. Commercially available systems for carrying out particle size analysis by laser diffraction are available from Clausthal-Zellerfeld, Germany (HELOS H1006).

Preferred drug delivery devices for particles are metered-dose inhalers. Metered-dose inhalers are described in Remington: The Science and Practice of Pharmacy, Twentieth Edition (Easton, Pa.: Mack Publishing Co., 2000) and in Ansel et al., Pharmaceutical Dosage Forms and Drug Delivery Systems, Sixth Edition (Malvern, Pa.: Lea & Febiger, 1995). The components of the drug delivery device, e.g., canister, housing, metering valve, etc., are commercially available. For example many components are available from 3M Corporation (St. Paul, Minn.). Typically, although not necessarily, the amount of pharmaceutical formulation (including polymer, solvents and other excipients) that is released per actuation of the drug delivery device is about 5 micrograms to about 100,000 micrograms of formulation.

The above formulations can also be administered following a physical therapy that aids mucociliary clearance. Such treatments include chest physiotherapy (manual or mechanical). Manual techniques include autogenic drainage and percussive techniques. Devices for mechanical therapy include positive expiratory pressure treatment, the "Flutter" mucus clearance device (a device that produces oscillations during exhalation), an inflatable vest driven by a pulsed-air delivery system.

In alternative embodiments, the variables for the compound used in the disclosed methods (represented by structural formula Ia) and the compound of the invention, represented by structural Ib, are as defined above, provided that the compounds are further characterized by one or more of the following features.

In one embodiment, the compound of the present invention and the compound of the method are represented by structural formula II, wherein Ring A is unsubstituted:

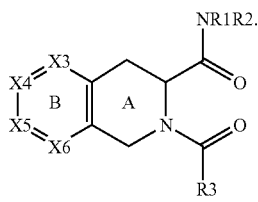

II

The variables for R1, R2, and R3 are as defined above for structural formula Ia or Ib. In a preferred embodiment, the variables R1, R2, and R3 are as disclosed in Table 1 below.

In Ring B, one of X3, X4, X5, and X6 can be N. Alternatively, X3 and X6 are —CH— and one of X4 or X5 is N. Preferably, X3, X4, X5, and X6 are —CH—, i.e., Ring B is as represented by structural formula III:

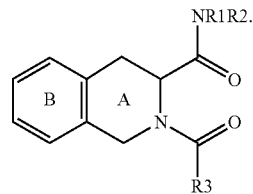

III

In a more preferred embodiment, R3 in structural formulas II and III is a six-membered aryl or heteroaryl group that is substituted and/or is fused to another ring. Examples include an optionally substituted 2-naphthyl, 6-(1,4 benzodioxan)yl, 6-indolyl, or 2-(9-fluorenon)yl group, or a substituted phenyl or pyridyl group. Here, appropriate substituents for the aryl or heteroaryl groups, or alternatively, the phenyl or pyridyl groups, include one or more groups selected from halogen, —CF$_3$, —NO$_2$, —CN, —R$^c$, —OR$^c$, and —XR$^f$, wherein R$^c$ is a C1-C5 branched or linear alkyl group. R$^f$ is an optionally substituted phenyl, pyridyl, N-pyridyl, N-morpholinyl, furanyl, thienyl, isoxazolyl, imidazolyl, pyrazolyl, pyrrolyl, pyrrolidyl, piperidyl, piperazyl, benzofuranyl, tetrazolyl, thiazolyl, tetrazolyl, benzothiazolyl, benzimidazolyl, cyclobutyl, cyclopentyl, or cyclohexyl group. Preferably, the group represented by R$^f$ is optionally substituted with one or more groups selected from halogen, —CF$_3$, —NO$_2$, —CN, —R$^c$, and —OR$^c$. X is —O—, —S—, —C(O)—, —S(O)—, —S(O$_2$)—, —CH$_2$—, —CH$_2$CH$_2$—, —OCH$_2$—, —OCH$_2$CH$_2$—, —SCH$_2$—, or —SCH$_2$CH$_2$—. Alternatively, X is —O—, —S—, —C(O)—, S(O)—, —CH$_2$—, —CH$_2$CH$_2$—, —OCH$_2$—, —OCH$_2$CH$_2$—, or more preferably —O—, —C(O)—, —S(O)—, or —CH$_2$—.

In another more preferred embodiment, in structural formula III, R1 is H; R2 is —X7-R6; and R3 is as described in the preceding paragraph. X7 is a covalent bond, or a C1-C12 alkyl chain (preferably a C1-C4 alkyl chain) optionally interrupted by —O— or —S—, and R6 is —SH, diphenylmethylene, or an optionally substituted 5 or 6 membered aryl, heteroaryl, heterocyclic, or C4 to C6 monocyclic cycloalkyl group. Alternatively, X7 is a covalent bond, or a C1-C4 alkyl chain optionally interrupted by —O— or —S—, and R6 is an optionally substituted phenyl, naphthyl, 3-quinolinyl, 6-quinolinyl, 2-thiazolyl, 2-furanyl. 5-indanyl, 2-(1,8-benzodiazin)yl, 6-(1,4-benzodioxan)yl, 5-(l1,3-benzodioxol)yl, 5-benzimidazolyl, 3-pyridyl, or a C4-C6 cycloalkyl group. More preferably, each cyclic group represented by R6 is optionally substituted with one or more groups selected from halogen, —CF$_3$, —R$^d$, —OR$^d$, —SR$^d$, —CO$_2$R$^d$, —COR$_d$, —OH, —SH, phenyl, phenoxyl, benzyl, benzoyl, N-morpholine, —NR$^d_2$, —NR$^d$COR$^e$, N-aniline, —NO$_2$, —CN, and C4-C6 cycloalkyl. Here, R$^d$ and R$^e$ are independently C1-C7 branched or linear alkyl groups.

In another preferred embodiment, in structural formula III, R1 and R2 are independently —H or an optionally substituted aliphatic, aryl, heteroaryl, heterocyclic, or monocyclic cycloalkyl group, provided that R1 and R2 are not both —H; or, R1 and R2, taken together with the nitrogen to which they are bonded, are an optionally substituted heterocyclic group. More preferably, R1 and R2 are as defined in the preceding paragraph. R3 is an optionally substituted 2-naphthyl, 6-(1,4 benzodioxan)yl, 6-indolyl, or 2-(9-fluorenon)yl group, or a phenyl or pyridyl group substituted with halogen, —CF$_3$, —NO$_2$, —CN, —R$^c$, —OR$^c$, or —XR$^f$, wherein R$^c$, X, and R$^f$ are as described above. Alternatively, the group represented by $R^f$ is optionally substituted with one or more groups selected from halogen, —$CF_3$, —$NO_2$, —CN, —$R^c$, and —$OR^c$. Preferably, R3 is a substituted phenyl or pyridyl group.

In still another embodiment, the compound of the present invention and the compound used in the disclosed methods are each represented by structural formula IV:

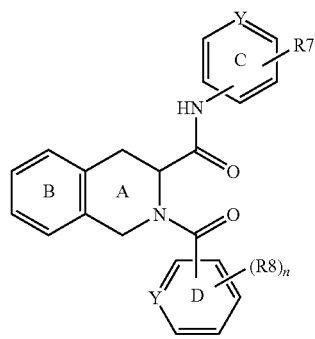

IV

Here each Y is independently —N— or —CH—. R7 is halogen, —$CF_3$, —$R^g$, —$OR^g$, —$SR^g$, —$CO_2R^g$, —$COR^g$, —OH, —SH, phenyl, phenoxyl, benzyl, benzoyl, N-morpholinyl, —$NR^g{}_2$, —$NR^gCOR^h$, N-aniline, —$NO_2$, —CN, or C4-C6 cycloalkyl, wherein n is 1 or 2. Each R8 is halogen, —$CF_3$, —$NO_2$, —CN, —$R^i$, —$OR^i$, or an optionally substituted phenoxy, phenyl sulfide, phenylsulfonyl, benzyl sulfide, benzyl, benzyloxy, benzoyl, —O-pyridyl, —$CH_2$-N-morpholine, —$OCH_2CH_2$-N-morpholine, cyclohexyloxy, or cyclopentyloxy group. Each $R^g$, $R^h$, and $R^i$ is independently a C1-C8 branched or linear alkyl group. Preferably, n is 1 and R7 is halogen, —$CF_3$, —$R^g$, —$OR^g$, —$SR^g$, —$COR^g$, —OH, —SH, phenyl, phenoxyl, benzyl, benzoyl, N-morpholinyl, —$NR^g{}_2$, —$NR^gCOR^h$, N-aniline, —$NO_2$, —CN, or C4-C6 cycloalkyl.

In still another embodiment, the compound of the present invention and the compound used in the disclosed methods are each represented by structural formula V:

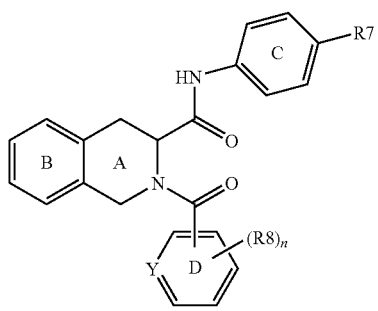

V

R7 is —$R^j$, $NR^j(CO)R^k$, or halogen, and each R8 is independently phenoxy, benzyloxy, C4-C6 cycloalkoxy, halogen, methoxy, ethoxy, 2-propyloxy, tert-butyloxy, 2-butyloxy, 3-pentyloxy, or methyl, while n is 1 or 2. $R^j$ is a C4-C8 linear alkyl group and $R^k$ is a C1-C4 branched or linear alkyl group.

In still another embodiment, the disclosed compound is represented by the following structural formula VI:

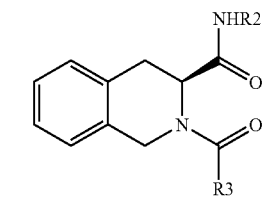

VI

R3) is represented by structural formula $R3^a$:

$R3^a$ and R2 is represented by one of structural formulas $R_2{}^a$ to $R2^c$:

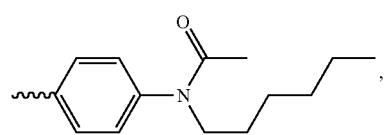

$R2^a$ $R2^b$ $R2^c$

Alternatively, R2 is represented by structural formula $R2^d$:

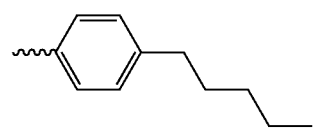

$R2^d$ and R3 is represented by one of structural formulas $R3^a$ or $R3^b$ to $R3^v$:

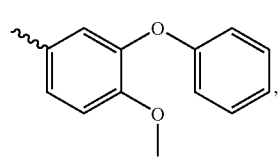

$R3^b$

-continued

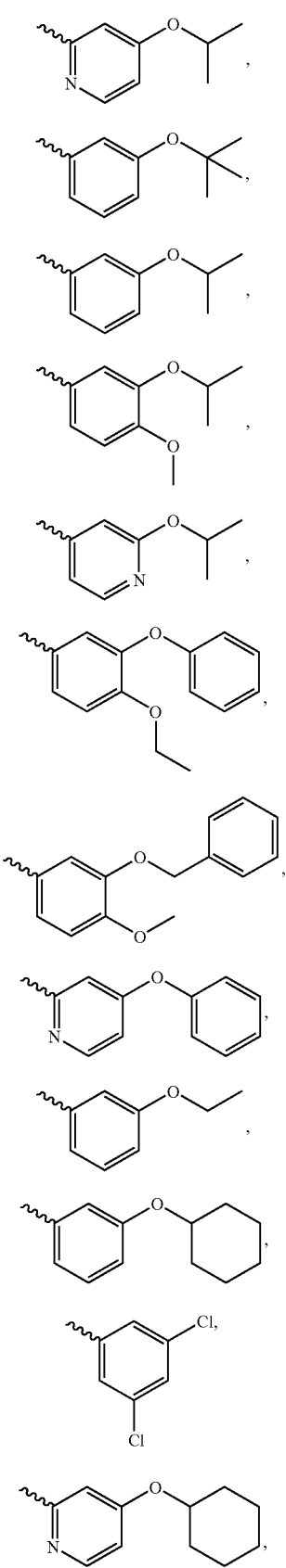

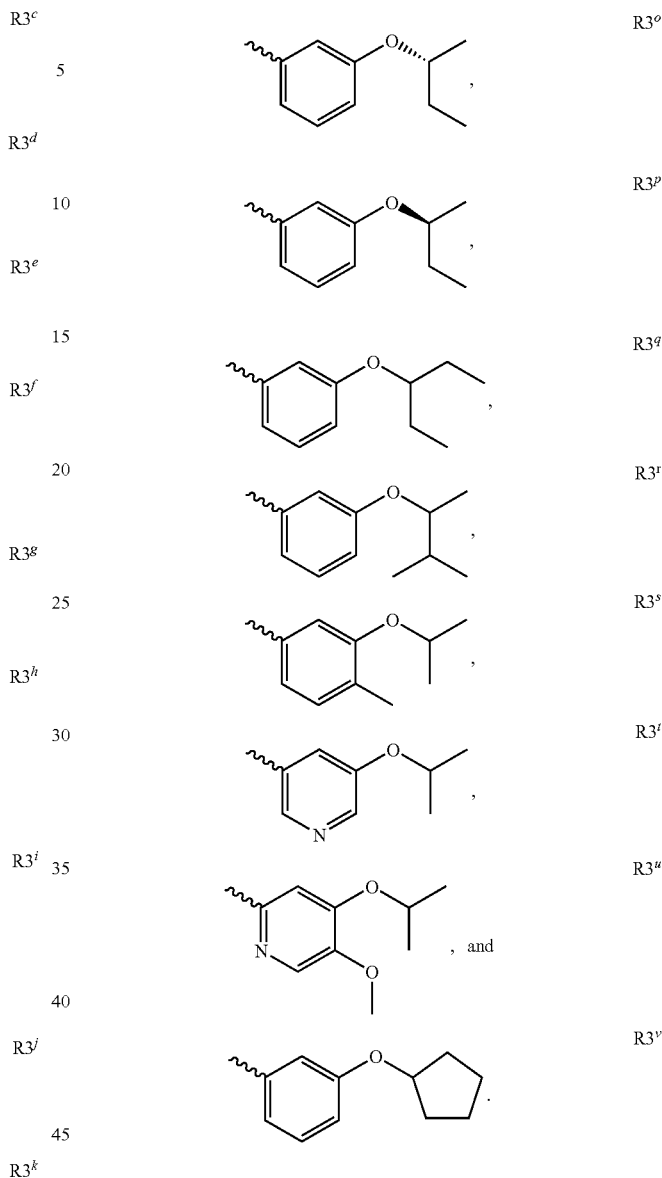

Alternatively, R2 is represented by one of structural formulas R2$^a$ to R2$^c$ and R3 is represented by structural formula R3$^a$. Alternatively, R2 is represented by structural formula R$_2$$^d$ and R3 is represented by one of structural formulas R3$^a$ to R3$^v$. Alternatively R2 is represented by structural formula R2$^a$ and R3 is represented by structural formula R3$^a$. Preferably, R2 is represented by structural formula R2$^d$; and R3 is represented by one of structural formulas R3$^a$ to R3$^g$.

EXEMPLIFICATION

The following Examples 1-20 illustrate chemical synthetic methods and intermediate compounds that can be used to make the disclosed compounds. In particular, each of the compounds listed in Table 1 was prepared by the indicated synthetic method or methods. In the following section, Examples 21-24 illustrate screening of the disclosed compounds for activity.

EXAMPLE 1

(±)-1,2,3,4-Tetrahydroisoquinoline-3-carboxylic acid (4-chlorophenyl)amide (Intermediate 1)

Step 1) Preparation of (±)-N-(tert-Butoxycarbonyl)-tetrahydroisoquinoline-3-carboxylic acid(4-chlorophenyl)amide To stirred solution of (±)-N-(tert-butoxycarbonyl)-1,2,3,4-tetrahydroisoquinoline-3-carboxylic acid (10.0 g, 3.61 mmol) in chloroform (180 mL) was added 1-[3-(dimethylamino)propyl]-3-ethylcarbodiimide hydrochloride (7.25 g, 37.8 mmol) followed by 4-chloroaniline (4.39 g, 34.4 mmol). After overnight stirring, the reaction mixture was washed with aqueous sodium bicarbonate solution, dried (sodium sulfate) and concentrated to afford crude product as a near colorless, foamy solid. This material was used in the next step without further purification.

Step 2) Preparation of Intermediate 1

To a stirred solution of the product of step I in methylene chloride (45 mL) was added trifluoroacetic acid (20 mL, 260 mmol). After 1.5 hours, more trifluoroacetic acid (5 mL, 65 mmol) was added and the reaction was stirred for an additional hour. At this time, the reaction was concentrated and the residue partitioned between ethyl acetate and aqueous sodium bicarbonate solution. The organic layer was dried (sodium sulfate) and concentrated to afford crude product as a beige solid. This material was purified by flash chromatography over silica (methylene chloride/methanol) followed by trituration with diethyl ether to afford 4.05 g (41%) of product as a fibrous white solid: $^1$H NMR (CDCl$_3$) δ 9.42 (s, 1H), 7.65-7.53 (m, 2H), 7.36-7.04 (m, 6H), 4.12-3.97 (m, 2H), 3.68 (dd, J=10.4, 5.4 Hz, 1H), 3.35 (dd, J=16.3. 5.4 Hz, 1H), 2.90 (dd, J=16.3, 10.4Hz, 1H) ppm.

EXAMPLE 2

(±)-2-(3-Phenoxybenzoyl)-1,2,3,4-tetrahydroisoquinoline-3-carboxylic acid (Intermediate 2)

Step 1) Preparation of (±)-2-(3-Phenoxybenzoyl)-1,2,3,4-tetrahydroisoquinoline-3-carboxylic acid ethyl ester To a stirred solution of (±)-1,2,3,4-tetrahydroisoquinoline-3-carboxylic acid ethyl ester (6.26 g, 30.5 mmol) and 3-phenoxybenzoic acid (7.19 g, 33.6 mmol) in chloroform (150 mL) was added 1-[3-(dimethylamino)propyl]-3-ethylcarbodiimide hydrochloride (6.43 g, 33.5 mmol). The reaction was allowed to proceed overnight and then washed with aqueous sodium bicarbonate solution, dried (sodium sulfate) and concentrated. The crude product was purified by flash chromatography over silica (hexanes/ethyl acetate) to afford 12.07 g (99%) of product as a colorless gum. In chloroform-d solvent, the proton NMR spectra of this compound appears as a 55:45 mixture of rotamers: $^1$H NMR (CDCl$_3$) δ 7.46-6.90 (m, 13H), 5.46 (t, J=5.6 Hz, 0.55H), 5.18 (d, J=17.6 Hz, 0.45H), 4.80-4.73 (m, 0.45H), 4.68-4.50 (m, 1.55H), 4.22-4.07 (m, 1.10H), 4.05-3.92 (m, 0.90H), 3.34-3.19 (m, 1.55H), 3.16-3.06 (m, 0.45H), 1.19 (t, J=7.1 Hz, 1.65H), 1.04 (t, J=7.1 Hz, 1.35H) ppm.

Step 2) Preparation of Intermediate 2

To a stirred solution of the product of step 1 (10.0 g, 2.50 mmol), in 1:1 ethanol/tetrahydrofuran (110 mL) was added 1.0 N aqueous sodium hydroxide solution (55 (mL). The mixture was stirred for 1 hour, concentrated and redissolved in water (150 (mL). While stirring, the solution was acidified with the addition of 1.0 N aqueous hydrochloric acid (55 mL). The resulting white precipitate was collected by filtration, rinsed with water and vacuum oven dried to afford 8.55 g (89%) of product as a white solid. In chloroform-d solvent, the proton NMR spectra of this compound appears as a 6:4 mixture of rotamers: $^1$H NMR (CDCl$_3$) δ 7.44-6.78 (m, 13H), 5.29 (t, J=5.7 Hz, 0.6H), 5.18 (d, J=17.9 Hz, 0.4H), 4.81-4.73 (m, 0.4H), 4.62-4.47 (m, 1.6H), 3.30-3.15 (m, 1.6H), 3.13-3.01 (m, 0.4H) ppm.

EXAMPLE 3

(S)-1,2,3,4-Tetrahydroisoquinoline-3-carboxylic acid (4-pentylphenyl)amide (Intermediate 3)

Step 1) Preparation of (S)—N-(tert-Butoxycarbonyl)-1,2,3,4-tetrahydroisoquinoline-3-carboxylic acid(4-pentylphenyl)amide To a stirred solution of (S)—N-(tert-butoxycarbonyl)-1,2,3,4-tetrahydroisoquinoline-3-carboxylic acid (10.0 g, 36.1 mmol) and 4-pentylaniline (4.91 g, 30.1 mmol) in chloroform (150 mL) was added 1-[3-(dimethylamino)propyl]-3-ethylcarbodiimide hydrochloride (6.92 g, 36.1 mmol). The reaction was allowed to proceed overnight and then washed with aqueous sodium bicarbonate solution, dried (sodium sulfate) and concentrated to afford crude product as an off-white, foamy solid. This material was used in the next step without further purification.

Step 2) Preparation of Intermediate 3

The product of step 1 was dissolved in methylene chloride (40 mL) and treated with trifluoroacetic acid (20 mL). After stirring for 2.5 hours the reaction was concentrated and the residue was partitioned between methylene chloride and aqueous sodium bicarbonate solution. The organic layer was removed and the aqueous layer was further basified with concentrated ammonium hydroxide (ca., 20 mL) and extracted with additional methylene chloride. The combined organic layers were dried (sodium sulfate) and concentrated. The resulting tacky, golden solid was triturated with diethyl ether and vacuum oven dried to afford 8.34 g (86%) of product as colorless platelets: $^1$H NMR (CDCl$_3$) δ 9.25 (s, 1H), 7.54-7.48 (m, 2H), 7.26-7.04 (m, 6H), 4.10-3.98 (m, 2H), 3.67 (dd, J=10.4, 5.5 Hz, 1H), 3.35 (dd, J=16.4, 5.5 Hz, 1H), 2.90 (dd, J=16.4, 10.4 Hz, 1H), 2.57 (t, J=7.6 Hz, 2H), 1.64-1.54 (m, 2H), 1.39-1.24 (m, 4H), 0.88 (t, J=6.8 Hz 3H) ppm.

Synthetic Method 1

EXAMPLE 4

(±)-2-(Naphthalene-2-carbonyl)-1,2,3,4-tetrahydroisoquinoline-3-carboxylic acid(4-chlorophenyl)amide (Compound 22)

Into a 10×75 mm test tube was loaded a methanolic solution (100 µL) of 2-naphthoic acid (25 µmol). Solvent was removed under a current of nitrogen. To the resulting residue was added a freshly prepared, methylene chloride solution (600 µL) of intermediate 1 (38 µmol), 1-[3-(dimethylamino)propyl]-3-ethylcarbodiimide hydrochloride (25 µmol) and 4-(dimethylamino)pyridine (2.6 µmol). The reaction vessel was sealed and agitated overnight. The reaction was then evaporated under nitrogen and partitioned between ethyl acetate and aqueous sodium bicarbonate solution. The organic layer was washed with water and concentrated under nitrogen to afford crude product. This material was used for biological testing without further purification.

Synthetic Method 2

EXAMPLE 5

(±)-2-(3-Phenoxybenzoyl)-1,2,3,4-tetrahydroisoquinoline-3-carboxylic acid[2-(4-bromophenyl)-ethyl]amide (Compound 73)

Into a 10×75 mm test tube was loaded a methanolic solution (50 µL) of 4-bromophenethyl amine (25 µmol). Solvent was removed under a current of nitrogen. To the resulting residue was added a freshly prepared, methylene chloride solution (600 µL) of intermediate 2 (28 µmol), 1-[3-(dimethylamino)propyl]-3-ethylcarbodiimide hydrochloride (25 µmol) and 4-(dimethylamino)pyridine (2.8 µmol). The reaction vessel was sealed and mixed by agitation overnight. The reaction was then evaporated under nitrogen and partitioned between ethyl acetate and aqueous sodium bicarbonate solution. The organic layer was washed with water and concentrated under nitrogen to afford crude product. This material was used for biological testing without further purification.

Synthetic Method 3

EXAMPLE 6

(S)-2-(3-Phenoxybenzoyl)-1,2,3,4-tetrahydroisoquinoline-3-carboxylic acid(6-pentylpyridin-3-yl)amide (Compound 107)

Synthetic method 3 is a general procedure whereby a commercially available or known monoprotected amino acid was carried through a three-step sequence consisting of: 1) an amide coupling reaction, 2) amine or acid deprotection and 3) a second amide coupling reaction. Intermediates were not purified. The final product was isolated by chromatography. This method is exemplified by the preparation of Compound 107.

Step 1) Preparation of (S)—N-(tert-Butoxycarbonyl)-1,2,3,4-tetrahydroisoquinoline-3-carboxylic acid(6-pentylpyridin-3-yl)amide To a stirred solution of (S)—N-(tert-butoxycarbonyl)-1,2,3,4-tetrahydroisoquinoline-3-carboxylic acid (0.666 g, 2.40 mmol) and 3-amino-6-pentylpyridine (0.330 g, 2.01 mmol) in chloroform (10 mL) was added 1-[3-(dimethylamino)propyl]-3-ethylcarbodiimide hydrochloride (0.460 g, 2.40 mmol) and a catalytic amount of 4-(dimethylamino)pyridine. The reaction was allowed to proceed overnight and then partitioned between methylene chloride and aqueous sodium bicarbonate solution. The organic layer was dried (sodium sulfate) and concentrated to afford a faint green foam.

Step 2) Preparation of (S)-1,2,3,4-Tetrahydroisoquinoline-3-carboxylic acid(6-pentylpyridin-3-yl)amide The crude product from step 1 was dissolved in methylene chloride (6.4 mL) and treated with trifluoroacetic acid (3.6 mL). After stirring for 1.5 hours the reaction was concentrated and the residue was partitioned between methylene chloride and aqueous sodium bicarbonate solution. The organic layer was dried (sodium sulfate) and concentrated to afford a gray-green solid.

Step 3) Preparation of Compound 107

To a stirred solution of the product of step 2 and 3-phenoxybenzoic acid (0.514 g, 2.40 mmol) in chloroform (10 mL) was added 1-[3-(dimethylamino)propyl]-3-ethylcarbodiimide hydrochloride (0.460 g, 2.40 mmol) and a catalytic amount of 4-(dimethylamino)pyridine. The reaction was allowed to proceed overnight and then worked up as in step 1. The resulting pale green solid was purified by flash chromatography (methylene chloride/methanol) to afford 0.704 g (67% overall) of product as a pale amber, foamy solid. In chloroform-d solvent, the proton NMR spectra of this compound appears as an 8:2 mixture of rotamers: $^1$H NMR (CDCl$_3$) δ 9.26 (s, 1H), 8.51 (s, 0.8H), 8.41-8.25 (m, 0.2H), 7.93 (d, J=7.3 Hz, 0.8H), 7.77-7.65 (m, 0.2H), 7.48-6.83 (m, 14H), 5.19 (t, J=6.7 Hz, 0.8H), 5.19-5.02 (m, 0.2H), 4.83-4.74 (m, 0.2H), 4.62 (d, J=15.2 Hz, 0.8H), 4.53-4.38 (m, 1H), 3.55-3.39 (m, 1H), 3.21-2.97 (m, 1B), 2.80-2.65 (m, 2H), 1.74-1.59 (m, 2H), 1.40-1.23 (m, 4H), 0.88 (t, J=6.5 Hz, 3H) ppm.

Synthetic Method 4

EXAMPLE 7

(+)-2-(3-Benzyloxybenzoyl)-1,2,3,4-tetrahydroisoquinoline-3-carboxylic acid(4-chlorophenyl)amide (Compound 14)

To a stirred solution of intermediate 1 (0.287 g, 1.00 mmol) and 3-benzyloxybenzoic acid (0.274 g, 1.20 mmol) in chloroform (5 mL) was added 1-[3-(dimethylamino)propyl]-3-ethylcarbodiimide hydrochloride (0.230 g, 1.20 mmol) and a catalytic amount of 4-(dimethylamino)pyridine. The reaction was allowed to proceed overnight and then partitioned between methylene chloride and aqueous sodium bicarbonate solution. The organic layer was dried (sodium sulfate) and concentrated to afford crude product. This material was purified by flash chromatography over silica (methylene chloride/methanol) to afford 0.485 g (98%) of product as a colorless foamy solid. In chloroform-d solvent, the proton NMR spectra of this compound appears as an 8:2 mixture of rotamers: $^1$H NMR (CDCl$_3$) δ 9.20 (s, 0.8H), 8.16 (br s, 0.2H), 7.58-6.83 (m, 17H), 5.32-5.19 (m, 0.8H), 5.16-4.87 (m, 2H), 4.83-4.71 (m, 0.2H), 4.67-4.48 (m, 1H), 4.44-4.25 (m, 1H), 3.63-3.34 (m, 1H), 3.22-2.95 (m, 1H) ppm.

Synthetic Method 5

EXAMPLE 8

(±)-2-(3-Phenoxybenzoyl)-1,2,3,4-tetrahydroisoquinoline-3-carboxylic acid(4-heptylphenyl)amide (Compound 94)

To a stirred solution of intermediate 2 (0.336 g, 0.900 mmol) and 4-heptylaniline (0.143 g, 0.747 mmol) in chloroform (5 mL) was added 1-[3-(dimethylamino)propyl]-3-ethylcarbodiimide hydrochloride (0.172 g, 0.897 mmol) and a catalytic amount of 4-(dimethylamino)pyridine. The reaction was allowed to proceed overnight and then partitioned between methylene chloride and aqueous sodium bicarbonate solution. The organic layer was dried (sodium sulfate) and concentrated to afford crude product. This material was purified by flash chromatography over silica (methylene chloride/methanol) to afford 0.352 g (86%) of product as a colorless foamy solid. In chloroform-d solvent, the proton NMR spectra of this compound appears as an 8:2 mixture of rotamers: $^1$H MR (CDCl$_3$) δ 8.81 (s, 0.8H), 7.54 (br s, 0.2H), 7.51-6.74 (m, 17H), 5.27 (t, J=6.4 Hz, 0.8H), 5.16 (d, J=16.5 Hz, 0.2H), 4.85-4.74 (m, 0.2H), 4.72-4.52 (m, 1H), 4.44-4.31 (m, 0.8H), 3.65-3.52 (m, 0.8H), 3.51-3.37 (m, 0.2H), 3.19-3.03 (m, 1H), 2.55 (t, J=7.6 Hz, 2H), 1.64-1.49 (m, 2H), 1.35-1.12 (m, 8H), 0.87 (t, J=6.6 Hz, 3H) ppm.

Synthetic Method 6

EXAMPLE 9

(S)-2-(3-Isopropoxybenzoyl)-1,2,3,4-tetrahydroisoquinoline-3-carboxylic acid(4-pentylphenyl)amide (Compound 130)

To a stirred solution of intermediate 3 (0.242 g, 0.750 mmol) and 3-isopropoxybenzoic acid (0.143 g, 0.747 mmol) in chloroform (4 mL) was added 1-[3-(dimethylamino)propyl]-3-ethylcarbodiimide hydrochloride (0.173 g, 0.902 mmol). The reaction was allowed to proceed overnight and then concentrated and partitioned between ethyl acetate and aqueous 1 N hydrochloric acid. The organic layer was washed with aqueous sodium bicarbonate solution, dried (sodium sulfate) and concentrated to afford crude product. This material was purified by flash chromatography over silica (methylene chloride/methanol) to afford 0.296 g (81%) of product as a colorless foamy solid. In chloroform-d solvent, the proton NMR spectra of this compound appears as an 8:2 mixture of rotamers: $^1$H NMR (CDCl$_3$) δ 8.95 (s, 0.8H), 7.99 (br s, 0.2H), 7.56-6.77 (m, 12H), 5.31 (t, J=6.6 Hz, 0.8H), 5.22 (d, J=15.7 Hz, 0.2H), 4.86-4.78 (m, 0.2H), 4.69-4.34 (m, 2.8H), 3.64-3.52 (m, 0.8H), 3.5103.37 (m, 0.2H), 3.20-3.00 (m, 1H), 2.55 (t, J=7.6 Hz, 2H), 1.63-1.50 (m, 2H), 1.39-1.18 (m,

Synthetic Method 7

EXAMPLE 10

(±)-2-(3-Phenoxybenzoyl)-1,2,3,4-tetrahydroisoquinoline-3-carboxylic acid[4-(acetylhexylamino)phenyl]amide (Compound 90)

Step 1) Preparation of N-(4-Aminophenyl)-N-hexylacetamide

To a stirred solution of 4'-aminoacetanilide (1.00 g, 6.66 mmol) in N,N-dimethylformamide (10 mL) was added sodium hydride (60% dispersion in mineral oil; 0.28 g, 7.0 mmol). After 5-10 minutes, 1-bromohexane was added dropwise to the mixture. The reaction was stirred for one hour and then partitioned between ethyl acetate and water. The organic layer was washed with additional water, dried (sodium sulfate) and concentrated. The resulting brown oil was purified by flash chromatography over silica (methylene chloride/methanol) to afford 1.32 g (84%) of product as a viscous amber oil: $^1$H NMR (CDCl$_3$) δ 6.91 (d, J=8.7 Hz, 1H), 6.68 (d, J=8.7Hz, 1H), 3.78 (br s, 2H), 3.61 (t, J=7.9Hz, 2H), 1.81 (s, 3H), 1.33-1.18 (m, 2H), 1.17-1.08 (m, 6H), 0.85 (t, J=6.9 Hz, 3H) ppm.

Step 2) Preparation of Compound 90

The product of step I was subjected to amide coupling with intermediate 2 according to the procedure described in synthetic method 5 to afford product as a colorless foamy solid. In chloroform-d solvent, the proton NMR spectra of this compound appears as an 8:2 mixture of rotamers: $^1$H NMR (CDCl$_3$) δ 9.27 (s, 0.8H), 8.33 (br s, 0.2H), 7.66-6.81 (m, 17H), 5.34-5.09 (m, 1H), 4.90-4.79 (m, 0.2H), 4.67-4.35 (m, 1.8H), 3.71-3.41 (m, 3H), 3.24-3.00 (m, 1H), 1.80 (s, 0.8H), 1.74 (s, 0.2H), 1.54-1.36 (m, 2H), 1.33-1.10 (m, 6H), 0.85 (t, J=6.9 Hz, 3H) ppm.

Synthetic Method 8

EXAMPLE 11

(±)-2-(3-Phenoxybenzoyl)-1,2,3,4-tetrahydroisoquinoline-3-carboxylic acid[4-(butyrylmethylamino)-phenyl]amide (Compound 95)

Step 1) Preparation of N-Methyl-N-(4-nitrophenyl)butyramide

To a stirred solution of butyryl chloride (0.770 g, 7.23 mmol) in chloroform (15 mL) was added N-methyl-4-nitroaniline and triethylamine (1.2 mL, 8.6 mmol). After overnight stirring, additional butyryl chloride (0.40 mL, 3.9 mmol) was added and the reaction was refluxed for 2-3 hours. The reaction was concentrated and the residue partitioned between ethyl acetate and aqueous sodium bicarbonate solution. The organic layer was combined with a second ethyl acetate extract, dried (sodium sulfate) and concentrated. The resulting dirty yellow oil was purified by flash chromatography over silica (methylene chloride/methanol) to afford 1.11 g (76%) of product as a pale yellow solid: $^1$H NMR (CDCl$_3$) δ 8.30 (d, J=8.9 Hz, 1H), 7.40 (d, J=8.9 Hz, 1H), 3.34 (s, 3H), 2.18 (t, J=7.5 Hz, 2H), 1.71-1.59 (m, 2H), 0.88 (t, J=7.6Hz, Step 2) Preparation of N-(4-Aminophenyl)-N-methylbutyramide To a stirred solution of the product of step 1 (1.08 g, 4.88 mmol) in ethanol (20 mL) was added 10% palladium on activated carbon (0.100 g). The reaction vessel was evacuated and backfilled with nitrogen several times. After a final evacuation the reaction vessel was backfilled with hydrogen. After 3.5 hours the hydrogen atmosphere was removed and the mixture was filtered through Celite and concentrated to afford 0.97 g (100%) of product as an amber gum: $^1$H NMR (CDCl$_3$)

δ 6.93 (d, J=8.6 Hz, 1H), 6.68 (d, J=8.6 Hz, 1H), 3.78 (br s, 2H), 3.20 (s, 3H), 2.04 (t, J=7.3 Hz, 2H 1.63-1.52 (m, 2H), 0.82 (t, J=7.4 Hz, 3H) ppm.

Step 3) Preparation of Compound 95

The product of step 2 was subjected to amide coupling with intermediate 2 according to the procedure described in synthetic method 5 to afford product as a colorless foamy solid. In chloroform-d solvent, the proton NMR spectra of this compound appears as an 8:2 mixture of rotamers: $^1$H NMR (CDCl$_3$) δ 9.20 (s, 0.8H), 8.01 (br s, 0.2H), 7.64-6.82 (m, 17H), 5.28-5.11 (m, 1H), 4.89-4.79 (m, 0.2H), 4.62 (d, J=15.6 Hz, 1H), 4.40 (d, J=15.6 Hz, 0.8H), 3.63-3.53 (m, 1H), 3.28-3.09 (m, 1H), 3.22 (s, 3H), 2.03 (t, J=7.3 Hz, 2H), 1.64-1.51 (m, 2H), 0.82 (t, J=7.1 Hz, 3H) ppm.

Synthetic Method 9

EXAMPLE 12

(±)-2-[3-(2-Methoxyphenoxy)benzoyl]-1,2,3,4-tetrahydroisoquinoline-3-carboxylic acid(4-chlorophenyl)amide (Compound 11)

A stirred mixture of 3-bromobenzonitrile (3.64 g, 20.0 mmol), 2-methoxyphenol (2.64 mL, 24.0 mmol), potassium carbonate (5.53g, 40.0 mmol) and copper(I) oxide (2.86 g, 36.0 mmol) in pyridine was heated at reflux for 2 days. The reaction was then partitioned between ethyl acetate and aqueous potassium hydrogen sulfate solution. The organic layer was dried (magnesium sulfate) and concentrated. The resulting crude product was partially purified by flash chromatography over silica (hexanes/ethyl acetate) to afford 4.40 g of a 9:1 mixture of product (92%) and 2-methoxyphenol. This material was used without further purification in the next step.

Step 2) Preparation of 3-(2-Methoxyphenoxy)benzoic acid

A mixture of the product of step 1 in ethylene glycol (10 mL) and 2 N aqueous potassium hydroxide (40 mL) was heated at reflux for 1 8 hours. The reaction solution was made acidic with concentrated hydrochloric acid and extracted with diethyl ether. The organic layer was dried (magnesium sulfate) and concentrated to afford crude product. This material was purified by triturating with diethyl ether/hexanes to afford 3.18 g(71%) of productasa white solid: $^1$H NMR (DMSO-d$_6$) δ 13.05 (s, 1H), 7.59 (d, J=7.9 Hz, 1H), 7.42 (t, J=7.9 Hz, 1H), 7.27-7.08 (m, 4H), 7.03-6.96 (m, 1H), 3.71 (s, 3H) ppm.

Step 3) Preparation of Compound 11

The product of step 3 was subjected to amide coupling with intermediate 1 according to the procedure described in synthetic method 4 to afford product as a white solid. In chloroform-d solvent, the proton NMR spectra of this compound appears as an 8:2 mixture of rotamers: $^1$H NMR (CDCl$_3$) δ 9.15 (s, 0.8H), 8.25 (br s, 0.2H), 7.5 1-6.74 (m, 16H), 5.20 (t, J=6.7 Hz, 0.8H), 5.16-5.03 (m, 0.2H), 4.86-4.77 (m, 0.2H), 4.62 (d, J=15.7 Hz, 0.8H), 4.39 (d, J=15.7 Hz, 1H), 3.80 (s, 0.8H), 3.69 (s, 0.2H), 3.57-3.36 (m, 1H), 3.20-2.91 (m, 1H) ppm.

Synthetic Method 10

EXAMPLE 13

(S)-2-(4-Cyclohexyloxypyridine-2-carbonyl)-1,2,3,4-tetrahydroisoquinoline-3-carboxylic acid(4-pentylphenyl)amide (Compound 119)

Step 1) Preparation of 4-Cyclohexyloxypyridine-2-carbonitrile

To a stirred solution of cyclohexanol (2.84 g, 3.00 mL, 2.84 mmol) in 1-methyl-2-pyrrolidinone (20 mL) was added sodium hydride (1.19 g of 60% dispersion, 29.8 mmol) in small portions over 5 minutes. After stirring for an additional 5 minutes, 2-chloro-4-cyanopyridine (3.75 g, 27.0 mmol) was added and the resulting red-brown solution was heated at 100° C. for 10 minutes. The reaction mixture then was poured onto ice. The mixture was diluted with water and extracted with ether. The combined organic phases were washed with water and brine, dried (magnesium sulfate) and concentrated to provide a yellow oil. Flash chromatography over silica (hexanes/ethyl acetate) afforded 4.17 g (76%) of the desired product as a cloudy oil which solidified on standing: $^1$H NMR (CDCl$_3$) δ 8.44 (d, J=5.8 Hz, 1H), 7.17 (d, J=2.4 Hz, 1H), 6.95 (dd, J=2.4, 5.8 Hz, 1H), 4.40-4.33 (m, 1H), 1.98-1.95 (m, 2H), 1.82-1.79 (m, 2H), 1.60-1.52 (m, 3H), 1.45-1.32 (m, 3H) ppm. $^{13}$C NMR (CDCl$_3$) δ 164.3, 152.2, 135.0, 117.3, 116.4, 113.9, 76.4, 31.1, 25.2, 23.4 ppm.

Step 2) Preparation of 4-Cyclohexylpyridine-2-carboxylic acid

A solution of the product of step 1 (4.17 g, 20.6 mmol) in ethanol (50 mL) was treated with sodium hydroxide solution (10 N, 20 mL) and heated to reflux. After 1 hour, the mixture was allowed to cool to room temperature and diluted with water. The solution was adjusted to pH 3 with concentrated hydrochloric acid and extracted with chloroform. The combined organic phases were washed with brine, dried (magnesium sulfate) and concentrated to provide 4.06 g (89%) of the desired product as a white solid: $^1$H NMR (CDCl$_3$) δ 14.3 (br s, 1H), 9.07 (d, J=6.3 Hz, 1H), 7.85 (d, J=2.3 Hz, 1H), 7.13 (dd, J=2.3, 6.3 Hz, 1H), 4.62-4.58 (m, 1H), 2.04-1.99 (m, 2H), 1.8201.78 (m, 2H), 1.65-1.57 (m, 3H), 1.47-1.28 (m, 3H) ppm. $^{13}$C NMR (CDCl$_3$) δ 169.8, 162.1, 150.1, 143.5, 114.3, 111.0, 78.0, 31.1, 25.0, 23.2 ppm.

Step 3) Preparation of Compound 119

The product of step 2 was subjected to amide coupling with intermediate 3 according to the procedure described in synthetic method 6 to afford product as a foamy white solid. In chloroform-d solvent, the proton NMR spectra of this compound appears as an 8:2 mixture of rotamers: $^1$H NMR of major rotamer (CDCl$_3$) δ 11.13 (s, 1H), 8.40 (d, J=5.8 Hz, 1H), 7.50 (d, J=8.3 Hz, 1H), 7.28 (d, J=2.4 Hz, 1H), 7.09-7.21 (m, 6H), 6.94 (dd, J=2.4, 5.Hz, 1H), 5.62 (d, J=17.3Hz, 1H), 5.10 (d, J=6.1 Hz, 1H), 4.46-4.41 (m, 1H), 4.27 (d, J=17.3 Hz, 1H), 3.40 (d, J=16.3 Hz, 1H), 2.92 (dd, J=6.1, 16.3 Hz, 1H), 2.55 (t, J=7.6 Hz, 2H), 2.05-1.92 (m, 2H), 1.85-1.75 (m, 2H), 1.65-1.55 (m, 5H), 1.52-1.27 (m, 7H), 0.87 (t, J=6.8 Hz, 3H) ppm. $^{13}$CNMR (CDCl$_3$) δ 167.8, 166.1, 155.2, 148.8, 138.8, 136.6, 132.6, 131.2, 129.1, 128.6, 127.2, 126.5. 126.4, 119.5, 113.6, 111.6, 76.3, 56.7, 42.1, 35.6, 31.6, 31.5, 29.3, 25.5, 23.7, 22.8, 14.3 ppm (note: 2 C signals appear to overlap).

Synthetic Method 11

EXAMPLE 14

(S)-2-(5-Cyclohexyloxypyridine-3-carbonyl)-1,2,3,4-tetrahydroisoquinoline-3-carboxylic acid(4-pentylphenyl)amide (Compound 131)

Step 1) Preparation of Methyl (5-cyclohexyloxy)nicotinate

To a stirred solution of methyl 5-hydroxynicotinate (2.40 g, 15.7 mmol) in methylene chloride (40 mL) was added cyclohexanol (1.73 g, 1.80 mL, 17.2 mmol) and triphenylphosphine (5.75 g, 21.9 mmol). The solution was treated with diethyl azodicarboxylate (3.20 mL, 20.4 mmol), resulting in a mild exotherm and development of an orange colored solution. The reaction mixture was allowed to stir at room temperature. After 16 hours, the cloudy yellow suspension was filtered, and the filtrate was washed with saturated sodium bicarbonate solution and brine, dried (magnesium sulfate), filtered, and concentrated to provide a yellow oil. Flash chromatography over silica (hexanes/ethyl acetate) afforded 1.08 g (29%) of the desired product as a colorless oil: $^1$H NMR (CDCl$_3$) δ 8.77 (d, J=1.7 Hz, 1H), 8.43 (d, J=2.9 Hz, 1H), 7.74 (dd, J=1.7, 2.9 Hz, 1H), 4.37-4.31 (m, 1H), 3.94 (s, 3H), 2.01-1.93 (m, 2H), 1.85-1.75 (m, 2H), 1.62-1.49 (m, 3H), 1.46-1.31 (m, 3H) ppm. $^{13}$C NMR (CDCl$_3$) δ 166.2, 154.0, 144.2, 142.9, 126.6, 122.3, 76.3, 52.7, 31.6, 25.6, 23.7 ppm.

Step 2) Preparation of 5-(Cyclohexyloxy)pyridine-3-carboxylic acid

To a solution of methyl (5-cyclohexyloxy)nicotinate (1.04 g, 4.40 mmol) in 3:1 methanol/water (20 mL) was added sodium hydroxide (0.203 g, 5.08 mmol). The reaction mixture was stirred at room temperature for 1 hour. The solution was then adjusted to pH 4 with 1N aqueous hydrochloric acid solution (5.1 mL). The resulting suspension was extracted with chloroform and the organic phase washed with brine, dried (magnesium sulfate), and concentrated to provide 0.915 g (94%) of the desired product as a white solid: $^1$H NMR (CDCl$_3$) δ 14.2 (br s, 1H), 8.94 (d, J=1.6 Hz, 1H), 8.55 (d, J=2.7 Hz, 1H), 7.98 (dd, J=1.6, 2.7 Hz, 1H), 4.46-4.39 (m, 1H), 2.04-196 (m, 2H), 1.86-1.76 (m, 2H), 1.64-1.53 (m, 3H), 1.47-1.32 (m, 3H) ppm. $^{13}$C NMR (CDCl$_3$) δ 168.0, 154.5, 141.6, 141.2, 128.4, 124.0, 76.3, 31.3, 25.4, 23.4 ppm.

Step 3) Preparation of Compound 131

The product of step 2 was subjected to amide coupling with intermediate 3 according to the procedure described in synthetic method 6 to afford product as a foamy white solid. In chloroform-d solvent, the proton NMR spectra of this compound appears as an 8:2 mixture of rotamers: $^1$H NMR of major rotamer (CDCl$_3$) δ 8.74 (br s, 1H), 8.39 (d, J=2.4 Hz, 1H), 8.22 (s, 1H), 7.44 (d, J=8.1 Hz, 2H), 7.30-7.20 (m, 4H), 7.12 (d, J 8.1 Hz, 2H), 6.97 (d, J=7.3 Hz, 1H), 5.24 (t, J=6.8 Hz, 1H), 4.59 (d, J=15.4 Hz, 1H), 4.47 (d, J=15.4 Hz, 1H), 4.38-4.25 (m, 1H), 3.60 (dd, J=6.8, 16.1 Hz, 1H), 3.18 (dd, J=6.8, 16.1 Hz, 1H), 2.57-2.53 (m, 2H), 2.02-1.92 (m, 2H), 1.84-1.76 (m, 2H), 1.62-1.50 (m, 5H), 1.40-1.24 (m, 7H), 0.89-0.86 (m, 3H) ppm. $^{13}$C NMR (CDCl$_3$) δ 170.1, 168.2, 154.1, 141.8, 139.5, 135.6, 134.1, 133.5, 131.6, 129.1, 128.5, 128.4, 127.0, 125.5, 120.8, 120.1, 76.5, 54.7, 48.6, 35.6, 31.6, 3.14, 29.3, 25.6, 23.7, 22.8, 14.3 ppm (note: 2 C signals appear to overlap).

Synthetic Method 12

EXAMPLE 15

(S)-2-[3-(3-Isopropoxy-4-methoxyphenoxy)benzoyl]-1,2,3,4-tetrahydroisoquinoline-3-carboxylic acid(4-pentyl-phenyl)amide (Compound 136)

Step 1) Preparation of 3-Isopropoxy-4-methoxybenzoic acid

To a stirred solution of methyl 3-hydroxy-4-methoxybenzoate (3.00 g, 16.5 mmol), isopropanol (1.9 mL, 24.8 mmol) and triphenylphosphine (5.40 g, 20.6 mmol) in ethyl acetate (70 mL) was added, dropwise, diethyl azodicarboxylate (3.9 mL, 25 mmol). The reaction was allowed to proceed overnight and then washed with aqueous sodium bicarbonate solution, dried (sodium sulfate) and concentrated. The resulting yellow oil was taken up in 1:1:1 tetrahydrofuran/methanol/1 N aqueous sodium hydroxide (120 mL) and heated at reflux. After 4 hours additional 1 N aqueous sodium hydroxide (10 mL) was added and the mixture was stirred at room temperature overnight. The reaction was then concentrated to remove organic solvents and diluted with water. After washing several times with ethyl acetate, the solution was stirred and acidified with 1 N aqueous hydrochloric acid (50 mL). The resulting precipitate was filtered off, rinsed with water and vacuum oven dried to afford 2.83 g (82%) of product as a white solid: $^1$H NMR (DMSO-d$_6$) δ 12.64 (s, 1H), 7.53 (dd, J=8.4, 1.8 Hz, 1H), 7.41 (d, J=1.8 Hz, 1H), 7.03 (d, J=8.4 Hz, 1H), 4.55 (sept, J=6.0 Hz, 1H), 3.71 (s, 3H) ppm.

Step 2) Preparation of Compound 136

The product of step 1 was subjected to amide coupling with intermediate 3 according to the procedure described in synthetic method 6 to afford product as a colorless foamy solid. In chloroform-d solvent, the proton NMR spectra of this compound appears as an 8:2 mixture of rotamers: $^1$H NMR (CDCl$_3$) δ 9.11 (br s, 0.8H), 8.64 (br s, 0.2H), 7.57-6.79 (m, 11H), 5.37-5.18 (m, 0.8H), 5.10-4.66 (m, 1.2H), 4.56-4.19 (m, 2H), 3.90 (s, 3H), 3.63-3.42 (m, 1H), 3.24-2.92 (m, 1H), 2.55 (t, J=7.5 Hz, 2H), 1.63-1.50 (m, 2H), 1.45-1.10 (m, 10H), 0.88 (t, J=6.8 Hz, 3H) ppm.

Synthetic Method 13

EXAMPLE 16

(S)-2-[3-(4-Ethoxy-3-phenoxyphenoxy)benzoyl]-1,2,3,4-tetrahydroisoquinoline-3-carboxylic acid (4-pentylphenyl)amide (Compound 121)

Step 1) Preparation of 4-Methoxy-3-phenoxybenzonitrile

Phenol and 3-bromo-4-methoxybenzonitrile were subjected to Ullman ether coupling according to the procedure described in synthetic method 9 to afford product as a white solid: $^1$H NMR (CDCl$_3$) δ 7.43 (dd, J=8.6, 2.0 Hz, 1H), 7.40-7.32 (m, 2H), 7.19-7.11 (m, 2H), 7.03 (d, J=8.6 Hz, 1H), 7.01-6.94 (m, 2H), 3.93 (s, 3H) ppm.

Step 2) Preparation of
4-Hydroxy-3-phenoxybenzonitrile

The product of step 1 (1.07 g, 4.75 mmol) was taken up in a 1 M methylene chloride solution of boron tribromide (20 mL, 20 mmol). After heating at reflux overnight the reaction was quenched by the dropwise addition of methanol (ca., 5 mL), and briefly refluxed. The mixture was then concentrated and the residue partitioned between ethyl acetate and aqueous sodium bicarbonate solution. The organic layer was dried (sodium sulfate) and concentrated to afford crude product as a brown solid. Flash chromatography over silica (hexanes/ethyl acetate) afforded 0.891 g (89%) of product a as a near colorless, crystalline solid: $^1$H NMR (CDCl$_3$) δ 7.42 (t, J=7.7 Hz, 2H), 7.32 (dd, J=8.3, 1.8 Hz, 1H), 7.23 (t, J=7.4 Hz, 1H), 7.12-7.01 (m, 4H), 6.29 (s, 1H) ppm.

Step 3) Preparation of
4-Ethoxy-3-phenoxybenzonitrile

To a stirred solution of the product of step 2 (0.742 g, 3.51 mmol), triphenylphosphine (1.01 g, 3.85 mmol) and ethanol (0.25 mL, 4.29 mmol) in ethyl acetate (12 mL) was added, dropwise, diethyl diazodicarboxylate (0.61 mL, 3.87 mmol). After 4 hours the reaction solution was diluted with ethyl acetate and washed with aqueous sodium bicarbonate solution. The organic layer was dried (sodium sulfate) and concentrated. The resulting gum was purified by flash chromatography over silica (hexanes/ethyl acetate) to afford 0.744 g (89%) of product as a white solid: $^1$H NMR (CDCl$_3$) δ7.40 (dd, J=8.4, 2.0 Hz, 1H), 7.37-7.31 (m, 2H), 7.17 (d, J=2.0 Hz, 1H), 7.13 (t, J=7.4 Hz, 1H), 7.03-6.92 (m, 3H), 4.13 (q, J=7.1 Hz, 2H), 1.37 (t, J=7.1 Hz, 3H) ppm.

Step 4) Preparation of 4-Ethoxy-
3-phenoxybenzoic acid

The product of step 3 (0.74 g, 3.09 mmol) was taken up in 2 N aqueous potassium hydroxide (50 mL) and ethylene glycol (7 mL). The mixture was heated at reflux overnight, cooled to room temperature and made acidic with the addition of concentrated aqueous hydrochloric acid (10 mL). The resulting precipitate was filtered off, rinsed with water and vacuum oven dried to afford 0.77 g (96%) of product as a white solid: $^1$H NMR (DMSO-d$_6$) δ 12.78 (br s, 1H), 7.74 (dd, J=8.6, 2.0 Hz, 1H), 7.41 (d, J=2.0 Hz, 1H), 7.34 (t, J=7.9 Hz, 2H), 7.22 (d, J=8.6 Hz, 1H), 7.08 (t, J=7.3 Hz, 1H), 6.90 (d, J=7.9 Hz, 2H) ppm.

Step 5) Preparation of Compound 121

The product of step 4 was subjected to amide coupling with intermediate 3 according to the procedure described in synthetic method 6 to afford product as a colorless glassy solid. In chloroform-d solvent, the proton NMR spectra of this compound appears as an 8:2 mixture of rotamers: $^1$H NMR (CDCl$_3$) δ 8.94 (br s, 0.8H), 7.86 (br s, 0.2H), 7.51-6.71 (m, 16H), 5.33-4.58 (m, 2H), 4.51-4.32 (m, 1H), 4.11 (q, J=7.0 Hz, 2H), 3.61-3.37 (m, 1H), 3.18-2.94 (m, 1H), 2.53 (t, J=7.3 Hz, 2 H), 1.62-1.49 (m, 2H), 1.34 (t, J=7.0 Hz, 3H), 1.35-1.22 (m, 4H), 0.88 (t, J=6.7 Hz, 3H) ppm.

Synthetic Method 14

EXAMPLE 17

(S)-2-[4-Methoxy-3-(2-morpholin-4-yl-ethoxy)benzoyl]-1,2,3,4-tetrahydroisoquinoline-3-carboxylic acid (4-pentylphenyl)amide (Compound 128)

Step 1) Preparation of
4-Methoxy-3-(2-morpholin-4-yl-ethoxy)benzoic acid methyl ester To stirred solution of methyl 3-hydroxy-4-methoxybenzoate (2.00 g, 11.0 mmol), 4-(2-hydroxyethyl)morpholine (1.58 g, 12.0 mmol) and triphenylphosphine (3.17 g, 12.1 mmol) in ethyl acetate (60 mL) was added, dropwise, diethyl azodicarboxylate (1.9 mL, 12.1 mmol). The reaction was allowed to proceed overnight and then diluted with additional ethyl acetate and extracted with 1 N aqueous hydrochloric acid. The aqueous layer was washed with ethyl acetate, basified with concentrated ammonium hydroxide and then extracted with ethyl acetate. The organic extract was dried (sodium sulfate) and concentrated to afford 3.25 g of a 92:8 mixture of product (95%) and diethyl hydrazinedicarboxylate as an amber oil. This material was used without further purification in the next step: $^1$H NMR (CDCl$_3$) δ 7.69 (dd, J=8.4, 2.0 Hz, 1H), 7.58 (d, J=2.0 Hz, 1H), 6.89 (d, J=8.4 Hz, 1H), 4.20 (t, J=6.0 Hz, 2H), 3.91 (s, 3H), 3.89 (s, 3H), 3.77-3.72 (m, 4H), 2.87 (t, J=6.0 Hz, 2H), 2.65-2.57 (m, 4H) ppm.

Step 2) Preparation of
4-Methoxy-3-(2-morpholin-4-yl-ethoxy)benzoic acid

To stirred solution of the product of step 1 (0.740 g, 2.5 1 mmol) in 1:1 tetrahydrofuran/methanol (20 mL) was added 1 N aqueous lithium hydroxide (5.0 mL, 5.0 mmol). The reaction was allowed to stir overnight and then treated with 1 N aqueous hydrochloric acid (5.0 mL, 5.0 mmol). The solution was concentrated with 1 N aqueous of crude product and sodium chloride as a tacky white solid. This material was used without further purification in the next step.

Step 3) Preparation of Compound 128

The product of step 2 was subjected to amide coupling with intermediate 3 according to the procedure described in synthetic method 6 to afford product as a colorless foamy solid. In chloroform-d solvent, the proton NMR spectra of this compound appears as an 8:2 mixture of rotamers: $^1$H NMR (CDCl$_3$) δ 9.00 (br s, 0.8H), 8.09 (br s, 0.2H), 7.54-6.80 (m, 11H), 5.37-4.60 (m, 2H), 4.55-4.34 (m, 1H), 4.08 (br s, 2H), 3.91 (s, 3H), 3.78-3.43 (m, 5H), 3.24-3.02 (m, 1H), 2.81 (br s, 2H), 2.64-2.40 (m, 6H), 1.64-1.50 (m, 2H), 1.38-1.22 (m, 4H), 0.88 (t, J=6.7 Hz, 3H) ppm.

Synthetic Method 15

EXAMPLE 18

(±)-threo and (±)-erythro-2-(3-Benzylbenzoyl)-4-methyl-1,2,3,4-tetrahydroisoquinoline-3-carboxylic acid(4-chlorophenyl)amide (Compound 18 and 19)

Step 1) Preparation of (±)-threo and (±)-erythro-4-Methyl-1,2,3,4-tetrahydroisoquinoline-3-carboxylic acid methyl ester To a stirred suspension of P-methyl-DL-phenylalanine hydrochloride (2.00 g, 9.27 mmol; approximately 2:1 mixture of threo and erythro diastereomers) in concentrated hydrochloric acid was added 37% aqueous formaldehyde solution (1.38 mL, 18.5 mmol). The mixture was heated at reflux for 1 hour, concentrated to dryness and redissolved in methanol (25 mL). Hydrogen chloride gas was bubbled through the solution for 10 minutes before refluxing overnight. The reaction was then concentrated and the residue partitioned between ethyl acetate and dilute aqueous ammonium hydroxide. The organic layer was dried (sodium sulfate) and concentrated to afford crude product as a yellow oil (1.00 g, 53%). This material was used in the next step without further purification.

Step 2) Preparation of (±)-threo and (±)-erythro-4-Methyl-2-(3-phenoxybenzoyl)-1,2,3,4-tetrahydroisoquinoline-3-carboxylic acid methyl ester To a stirred solution of the product of step I (combined with a second batch of similarly prepared material; 2.30 g, 11.2 mmol) and 3-phenoxybenzoic acid (2.44 g, 11.4 mmol) in methylene chloride was added 1-[3-(dimethylamino)propyl]-3-ethylcarbodiimide hydrochloride (2.19 g, 11.4 mmol) and a catalytic amount of 4-(dimethylamino)pyridine. After overnight stirring, the reaction mixture was washed with aqueous sodium bicarbonate solution, dried (magnesium sulfate) and concentrated. The resulting crude product was purified by flash chromatography over silica (hexanes/ethyl acetate) to afford 1.00 g (24%) of product as a white solid: $^1$H NNR (CDCl$_3$) δ 7.53-6.86 (m, 13H), 5.16-4.91 (m, 1H), 4.90-4.47 (m, 2H), 3.76-3.15 (m, 4H), 1.48 (d, J=7.0 Hz, 3H) ppm. MS (ES!) m/z 402 (M+H$^+$).

Step 3) Preparation of (±)-threo and (±)-erythro-4-Methyl-2-(3-phenoxybenzoyl)-1,2,3,4-tetrahydroisoquinoline-3-carboxylic acid To a stirred solution of the product of step 2 (combined with a second batch of similarly prepared material; 2.15 g, 5.36 mmol) in methanol (30 mL) was added 4N aqueous sodium hydroxide solution (10 mL). After overnight stirring, the reaction was concentrated to dryness. The residue was taken up in water, adjusted to approximately pH 2 with concentrated hydrochloric acid and extracted with methylene chloride. The organic extract was dried (magnesium sulfate) and concentrated. $^1$H NMR analysis of the resulting solid revealed the material to be a mixture of starting ester and product. The material was redissolved in 1:1 tetrahydrofuran/methanol (20 mL) and again treated with 4N aqueous sodium hydroxide (10 mL). After overnight stirring, the reaction was worked up as before to afford 1.30 g (63%) of product as a white solid. This material was used without further purification in the next step.

Step 4) Preparation of Compound 18 and 19

To a stirred solution of the product of step 3 (1.30 g, 3.36 mmol) and 4-chloroaniline (0.330 g, 2.60 mmol) in methylene chloride was added 1-[3-(dimethylamino)propyl]-3-ethylcarbodiimide hydrochloride (0.600 g, 3.13 mmol) and a catalytic amount of 4-(dimethylamino)pyridine. After overnight stirring, the reaction mixture was washed with aqueous sodium bicarbonate solution, dried (magnesium sulfate) and concentrated. The resulting solid was purified by flash chromatography over silica (hexanes/ethyl acetate) to yield the separated diastereomers of the product. The less polar diastereomer (Compound 18) was afforded as 0.54 g (32%) of an off-white solid. In chloroform-d solvent, the proton NMR spectra of this compound appears as a 3:1 mixture of rotamers: $^1$H NMR (CDCl$_3$) δ 9.12 (s, 0.75H), 8.47 (s, 0.25H), 7.53-6.79 (m, 17H), 5.20 (d, J=18.9 Hz, 0.25H), 4.89 (d, J=6.4 Hz, 0.75 H), 4.68-4.54 (m, 1H), 4.43 (d, J=15.7 Hz, 1H), 3.77-3.62 (m, 1H), 1.43 (d, J=7.1 Hz, 2.25H), 1.17 (d, J=7.1 Hz, 0.75H) ppm. MS (ESI) m/z 497 (M(Cl$^{35}$)+H$^+$).

The more polar diastereomer (Compound 19) was afforded as 0.45 g (27%) of an off-white solid: $^1$H NMR (CDCl$_3$) δ 8.79 (s, 1H), 7.50-6.66 (m, 17H), 5.26 (d, J=5.3 Hz, 1H), 4.68 (d, J=15.7 Hz, 1H), 4.63 (d, J=15.7 Hz, 1H), 3.34 (q, J=6.6 Hz, 1H), 1.53 (d, J=7.0 Hz, 3H) ppm. MS (ESI) m/z 497 (M(Cl$^{35}$)+H$^+$).

Synthetic Method 16

EXAMPLE 19

(S)-2-(4-Isopropoxy-5-methoxypyridine-2-carbonyl)-1,2,3,4-tetrahydroisoquinoline-3-carboxylic acid(4-pentylphenyl)amide (Compound 145)

Step 1) Preparation of 2-Hydroxymethyl-4-isopropoxy-5-methoxypyridine

To a stirred suspension of 2-hydroxymethyl-5-methoxy-4-pyridone (1.00 g, 6.45 mmol) in N,N-dimethylformamide (10 mL) was added sodium hydride (60% dispersion in mineral oil; 0.26 g, 6.5 mmol). The fizzy mixture was stirred for 5-10 minutes before adding, dropwise, 2-iodopropane (0.65 mL, 6.5 mmol). The reaction was stirred at room temperature overnight and then at reflux for 4 hours. At this time, additional sodium hydride (0.07 g, 1.8 mmol) and 2-iodopropane (0.16 mL, 1.6 mmol) were added and the mixture was heated at reflux for another 4 hours. The reaction was then concentrated and partitioned between methylene chloride and aqueous sodium carbonate solution. The resulting biphasic mixture was filtered through Celite to remove a small amount undissolved solid. The organic layer of the filtrate was dried (sodium sulfate) and concentrated to afford a dark brown oil. This material was purified by flash chromatography over silica (methylene chloride/methanol) to afford 410 g (32%) of product as a crystalline light brown solid: $^1$H NMR (CDCl$_3$) δ 7.92 (s, 1H), 6.61 (s, 1H), 4.54 (sept, J=6.2 Hz, 1H), 4.53 (s, 2H), 3.79 (s, 3H), 1.29 (d, J=6.0 Hz, 6H) ppm.

Step 2) Preparation of 4-Isopropoxy-5-methoxypyridine-2-carboxylic acid

To a stirred and heated (50° C.) solution of the product of step 1 (0.410 g, 2.08 mmol) in water (12 mL) was added, portionwise over 30 minutes, solid potassium permanganate (0.680 g, 4.30 mmol). Following the addition, reaction temperature was increased to 70° C. After 45 minutes the reaction was cooled to room temperature and treated with a solution of potassium hydroxide (0.230 g, 4.10 mmol) in water (6 mL) followed by a few drops of isopropanol. The mixture was stirred for about 5 minutes before filtering through Celite. The filtrate was concentrated to dryness under a nitrogen current. The resulting brown residue was dissolved in water (10 mL), adjusted to pH 2 with concentrated hydrochloric acid and extracted repeatedly with chloroform. The combined extracts were dried (sodium sulfate) and concentrated to afford 0.414 g (94%) of product as a pink-gray foam: $^1$H NMR (DMSO-d$_6$) δ 8.23 (s, 1H), 7.58 (s, 1H), 4.81 (sept, J=6.0 Hz, 1H), 3.90 (s, 3H), 1.29 (d, J=6.0 Hz, 6H) ppm.

Step 3) Preparation of Compound 145

The product of step 2 was subjected to amide coupling with intermediate 3 according to the procedure described in synthetic method 6 to afford product as an off-white foamy solid. In chloroform-d solvent, the proton NMR spectra of this compound appears as an 8:2 mixture of rotamers: $^1$H NMR of major rotamer (CDCl$_3$) δ 10.87 (s, 1H), 8.07 (s, 1H), 7.53-7.04 (m, 9H), 5.59 (d, J=17.3 Hz, 1H), 5.27 (d, J=6.0 Hz, 1H), 4.75 (sept, J=6.0 Hz, 1H), 4.29 (d, J=17.3 Hz, 1H), 4.00 (s, 3H), 3.43 (d, J=16.3 Hz, 1H), 2.93 (dd, J=16.3, 6.0 Hz, 1H), 2.55 (t, J=7.6 Hz, 6H), 1.63-1.52 (m, 2H), 1.46 (d, J=6.0 Hz, 1.5H), 1.43 (d, J=6.0 Hz, 1.5H), 1.36-1.23 (m, 4H), 0.87 (t, J=6.6 Hz, 3H) ppm.

Synthetic Method 17

EXAMPLE 20

(S)-2-(2-Isopropoxypyridine-4-carbonyl)-1,2,3,4-tetrahydroisoquinoline-3-carboxylic acid(4-pentylphenyl)amide (Compound 146)

Step 1) Preparation of 2-Isopropoxyisonicotinonitrile

To isopropanol (30.0 mL) was added sodium hydride (0.606 g of 60% dispersion, 15.2 mmol) in small portions over 5 minutes. The resulting gel-like suspension was stirred for an additional 5 minutes at room temperature. 2-Chloro-4-cyanopyridine (2.00 g, 14.4 mmol) was then added in one portion and the resulting solution was heated to reflux. After 1 hour, the reaction mixture was allowed to cool to room temperature. The mixture was diluted with water and extracted with ethyl acetate. The organic phase was washed with water and brine, dried (magnesium sulfate) and concentrated to provide a yellow oil. Flash chromatography over silica (hexanes/ethyl acetate) afforded 1.25 g (53%) of product as a colorless oil: $^1$H NMR (CDCl$_3$) δ 8.27 (d, J=5.2 Hz, 1H), 7.01 (dd, J=5.2, 1.4 Hz, 1H), 6.91 (d, J=1.4 Hz, 1H), 5.31 (sept, J=6.2 Hz, 1H), 3.33 (d, J=6.2 Hz, 6H) ppm.

Step 2) Preparation of 2-Isopropoxyisonicotinic acid

A solution of the product of step 1 (1.25 g, 7.71 mmol) in ethanol (20 mL) was treated with 10 N aqueous sodium hydroxide solution (10 mL) and heated to reflux. After 1 hour, the mixture was cooled to room temperature and diluted with water. Concentrated hydrochloric acid was added to attain pH=4, and the resulting precipitate was isolated by filtration. The material was washed with water and dried in vacuo to provide 0.920 g (66%) of product as a white solid: $^1$H NMR (CDCl$_3$) δ 12.1 (br s, 1H), 8.32 (d, J=5.2 Hz, 1H), 7.42 (dd, J=5.2, 1.4 Hz, 1H), 7.33 (d, J=1.4 Hz, 1H), 5.32 (sept, J=6.1 Hz, 1H), 1.37 (d, J=6.1 Hz, 6H) ppm. $^{13}$C NMR (CDCl$_3$) δ 170.0, 164.2, 147.9, 139.2, 115.4, 112.5, 68.9, 21.9 ppm.

Step 3) Preparation of Compound 146

The product of step 2 was subjected to amide coupling with intermediate 3 according to the procedure described in synthetic method 6 to afford product as a white solid. In chloroform-d solvent, the proton NMR spectra of this compound appears as an 8:2 mixture of rotamers: $^1$H NMR of major rotamer (CDCl$_3$) δ 8.67 (s, 1H), 8.24 (d, J=5.1 Hz, 1H), 7.42 (d, J=8.4 Hz, 2H), 7.30-7.29 (m, 2H), 7.22-7.10 (m, 3H), 6.95 (d, J=7.3 Hz, 1H), 6.78 (dd, J=5.1, 1.1 Hz, 1H), 6.68 (s, 1H), 5.34 (sept, J=6.2 Hz, 1H), 5.25 (t, J=7.0 Hz, 1H), 4.51 (d, J=15.4 Hz, 1H), 4.40 (d, J=15.4 Hz, 1H), 3.59 (dd, J=16.1, 7.0 Hz, 1H), 3.15 (dd, J=16.1, 7.0 Hz, 1H), 2.55 (t, J=7.7 Hz, 2H), 1.59-1.56 (m, 2H), 1.36 (d, J=6.2 Hz, 6H), 1.33-1.27 (m, 4H), 0.88 (t, J=6.9 Hz, 3H) ppm. $^{13}$C NMR (CDCl$_3$) δ 170.2, 167.8, 163.9, 147.9, 145.4, 139.1, 135.4, 133.8, 133.1, 128.8, 128.3, 128.1, 126.7, 125.2, 119.9, 113.4, 109.3, 68.7, 54.1, 48.0, 35.3, 31.4, 31.2, 29.0, 22.5, 22.0, 14.0 ppm.

TABLE 1

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

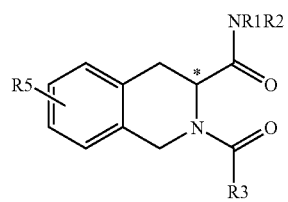

IIIa

| Compound # | Method | *R/S | R1NR2 | C(O)R3 | R5 |
|---|---|---|---|---|---|
| 1 | 3 | — | HN—C$_6$H$_4$—Cl | C(O)—C$_6$H$_4$—O—C$_6$H$_5$ | H |
| 2 | 3 | S | HN—C$_6$H$_4$—Cl | C(O)—C$_6$H$_4$—O—C$_6$H$_5$ | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

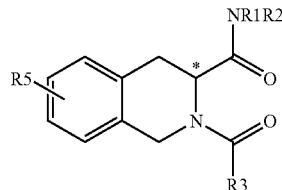

IIIa

| Compound # | Method | *R/S | R1NR2 | C(O)R3 | R5 |
|---|---|---|---|---|---|
| 3 | 4 | — | HN—C6H4—Cl | C(O)-fluorenone | H |
| 4 | 4 | — | HN—C6H4—Cl | C(O)-3-benzoylphenyl | H |
| 5 | 4 | — | HN—C6H4—Cl | C(O)-3-(4-chlorophenoxy)phenyl | H |
| 6 | 4 | — | HN—C6H4—Cl | C(O)-3-(4-methoxyphenoxy)phenyl | H |
| 7 | 4 | — | HN—C6H4—Cl | C(O)-3-(4-methylphenoxy)phenyl | H |
| 8 | 4 | — | HN—C6H4—Cl | C(O)-3-(4-tert-butylphenoxy)phenyl | H |
| 9 | 4 | — | HN—C6H4—Cl | C(O)-3-(3-trifluoromethylphenoxy)phenyl | H |
| 10 | 4 | — | HN—C6H4—Cl | C(O)-3-(4-fluorophenoxy)phenyl | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

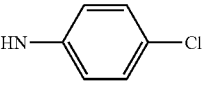

IIIa

| Compound # | Method | *R/S | R1NR2 | C(O)R3 | R5 |
|---|---|---|---|---|---|
| 11 | 9, 4 | — | 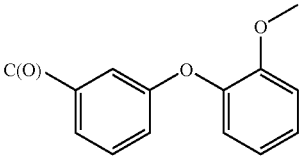 | 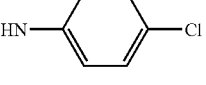 | H |
| 12 | 4 | — | 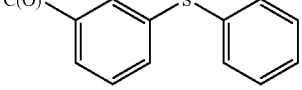 | 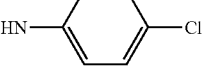 | H |
| 13 | 4 | — | 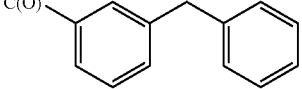 | 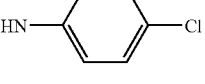 | H |
| 14 | 4 | — | 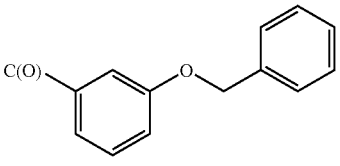 | 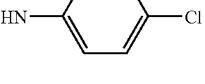 | H |
| 15 | 4 | — | 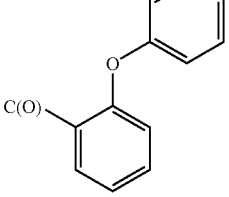 | 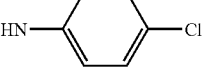 | H |
| 16 | 4 | — | 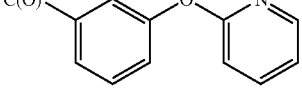 | 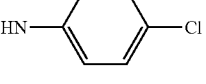 | H |
| 17 | 9, 4 | — | 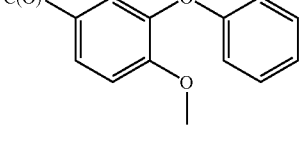 | 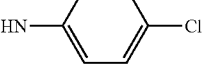 | H |
| 18 | 15 | * | 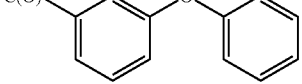 | | 4-CH$_3$ |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

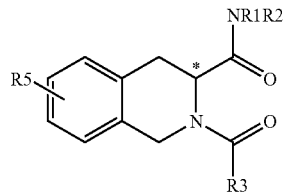

IIIa

| Compound # | Method | *R/S | R1NR2 | C(O)R3 | R5 |
|---|---|---|---|---|---|
| 19 | 15 | * | HN—⟨C6H4⟩—Cl | C(O)—⟨C6H4⟩—O—⟨C6H5⟩ | 4-CH$_3$ |
| 20 | 3 | — | HN—⟨C6H4⟩—Cl | C(O)—⟨C6H4⟩—O—⟨C6H5⟩ | 7-OH |
| 21 | 3 | — | HN—⟨C6H4⟩—(CH2)4CH3 | C(O)—⟨C6H4⟩—O—⟨C6H5⟩ | 5-CH$_3$ |
| 22 | 1 | — | HN—⟨C6H4⟩—Cl | C(O)—naphthyl | H |
| 23 | 1 | — | HN—⟨C6H4⟩—Cl | C(O)—(5-butylpyridin-2-yl) | H |
| 24 | 1 | — | HN—⟨C6H4⟩—Cl | C(O)—(7-azaindol-6-yl) | H |
| 25 | 2 | — | HN—⟨C6H4⟩—OCH3 | C(O)—⟨C6H4⟩—O—⟨C6H5⟩ | H |
| 26 | 2 | — | HN—CH(C6H5)2 | C(O)—⟨C6H4⟩—O—⟨C6H5⟩ | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

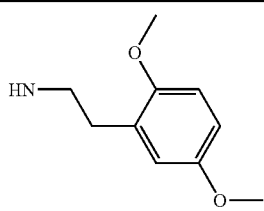

IIIa

| Compound # | Method | *R/S | R1NR2 | C(O)R3 | R5 |
|---|---|---|---|---|---|
| 27 | 2 | — | 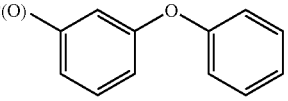 | 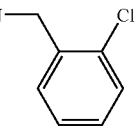 | H |
| 28 | 2 | — | 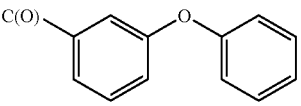 | 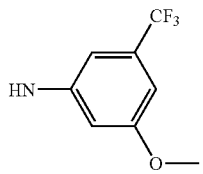 | H |
| 29 | 2 | — | 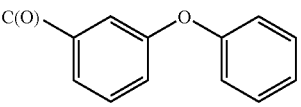 | 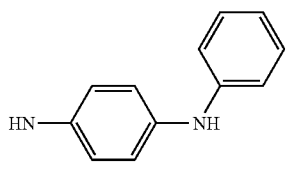 | H |
| 30 | 2 | — | 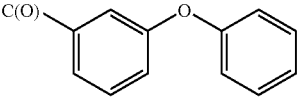 | 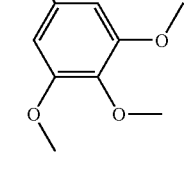 | H |
| 31 | 2 | — | 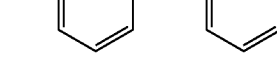 | 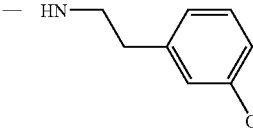 | H |
| 32 | 2 | — | 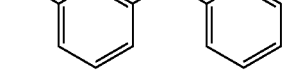 | 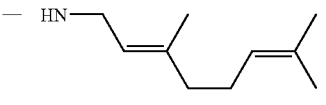 | H |
| 33 | 2 | — | 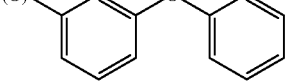 | 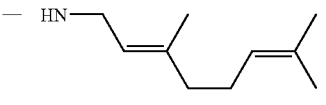 | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 34 | 2 | — | HN-C6H4-NHC(O)CH3 | C(O)-C6H4-O-C6H5 | H |
| 35 | 2 | — | HN-CH2-C6H4-Cl (4-Cl) | C(O)-C6H4-O-C6H5 | H |
| 36 | 2 | — | HN-CH2-C6H4-Cl (3-Cl) | C(O)-C6H4-O-C6H5 | H |
| 37 | 2 | — | HN-CH2-C6H4-OCH3 | C(O)-C6H4-O-C6H5 | H |
| 38 | 2 | — | HN-C6H4-C(O)OEt | C(O)-C6H4-O-C6H5 | H |
| 39 | 2 | — | HN-quinolin-6-yl | C(O)-C6H4-O-C6H5 | H |
| 40 | 2 | — | HN-quinolin-3-yl | C(O)-C6H4-O-C6H5 | H |
| 41 | 2 | — | HN-2,5-dimethoxyphenyl | C(O)-C6H4-O-C6H5 | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 42 | 2 | — | HN-(indanyl) | C(O)-(3-phenoxyphenyl) | H |
| 43 | 2 | — | HN-(3,4-dimethylphenyl) | C(O)-(3-phenoxyphenyl) | H |
| 44 | 2 | — | HN-(3,5-di-tert-butylphenyl) | C(O)-(3-phenoxyphenyl) | H |
| 45 | 2 | — | HN-(4-phenoxyphenyl) | C(O)-(3-phenoxyphenyl) | H |
| 46 | 2 | — | HN-(4-methylthiophenyl) | C(O)-(3-phenoxyphenyl) | H |
| 47 | 2 | — | HN-(5-methyl-2-methoxyphenyl) | C(O)-(3-phenoxyphenyl) | H |
| 48 | 2 | — | HN-(3,4,5-trimethoxyphenyl) | C(O)-(3-phenoxyphenyl) | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

| Compound # | Method | *R/S | R1NR2 | C(O)R3 | R5 |
|---|---|---|---|---|---|
| 49 | 2 | — | HN-C6H4-morpholine | C(O)-C6H4-O-C6H5 | H |
| 50 | 2 | — | HN-C6H4-N(CH3)2 | C(O)-C6H4-O-C6H5 | H |
| 51 | 2 | — | HN-3,5-dimethoxyphenyl | C(O)-C6H4-O-C6H5 | H |
| 52 | 2 | — | HN-benzodioxane | C(O)-C6H4-O-C6H5 | H |
| 53 | 2 | — | HN-C6H4-C(O)OCH3 | C(O)-C6H4-O-C6H5 | H |
| 54 | 2 | — | HN-(2,4-dimethyl-1,8-naphthyridinyl) | C(O)-C6H4-O-C6H5 | H |
| 55 | 2 | — | HN-biphenyl | C(O)-C6H4-O-C6H5 | H |
| 56 | 2 | — | HN-C6H4-C(O)CH3 | C(O)-C6H4-O-C6H5 | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 57 | 2 | — | HN-(2-methoxycarbonylphenyl) | C(O)-(3-phenoxyphenyl) | H |
| 58 | 2 | — | HN-(3-bromophenyl) | C(O)-(3-phenoxyphenyl) | H |
| 59 | 2 | — | HN-(4-chloro-3-methylphenyl) | C(O)-(3-phenoxyphenyl) | H |
| 60 | 2 | — | HN-CH2CH2-SH | C(O)-(3-phenoxyphenyl) | H |
| 61 | 2 | — | HN-(4-cyanophenyl) | C(O)-(3-phenoxyphenyl) | H |
| 62 | 2 | — | HN-(benzo[1,3]dioxol-5-yl) | C(O)-(3-phenoxyphenyl) | H |
| 63 | 2 | — | HN-(5-methylthiazol-2-yl) | C(O)-(3-phenoxyphenyl) | H |
| 64 | 2 | — | HN-(1H-benzimidazol-5-yl) | C(O)-(3-phenoxyphenyl) | H |
| 65 | 2 | — | HN-(3-methoxyphenyl) | C(O)-(3-phenoxyphenyl) | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 66 | 2 | — | HN—(3-ethoxycarbonyl-phenyl) | C(O)-(3-phenoxyphenyl) | H |
| 67 | 2 | — | HN—(4-methylphenyl) | C(O)-(3-phenoxyphenyl) | H |
| 68 | 2 | — | HN—CH2CH2-phenyl | C(O)-(3-phenoxyphenyl) | H |
| 69 | 2 | — | HN—CH2-(4-methylphenyl) | C(O)-(3-phenoxyphenyl) | H |
| 70 | 2 | — | HN—CH2CH2—S—CH2-(2-furyl) | C(O)-(3-phenoxyphenyl) | H |
| 71 | 2 | — | HN—CH2CH2—S—CH2-(2-fluoro-6-chlorophenyl) | C(O)-(3-phenoxyphenyl) | H |
| 72 | 2 | — | HN—CH2CH2—S—CH2-(2,6-dichlorophenyl) | C(O)-(3-phenoxyphenyl) | H |
| 73 | 2 | — | HN—CH2-(4-bromophenyl) | C(O)-(3-phenoxyphenyl) | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

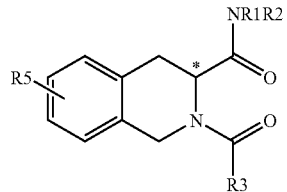

IIIa

| Compound # | Method | *R/S | R1NR2 | C(O)R3 | R5 |
|---|---|---|---|---|---|
| 74 | 2 | — | HN-cyclobutyl | C(O)-phenyl-O-phenyl | H |
| 75 | 2 | — | HN-(4-propylphenyl) | C(O)-phenyl-O-phenyl | H |
| 76 | 2 | — | HN-(4-cyclohexylphenyl) | C(O)-phenyl-O-phenyl | H |
| 77 | 2 | — | HN-(4-sec-butylphenyl) | C(O)-phenyl-O-phenyl | H |
| 78 | 2 | — | HN-(4-isopropylphenyl) | C(O)-phenyl-O-phenyl | H |
| 79 | 2 | — | HN-(4-ethylphenyl) | C(O)-phenyl-O-phenyl | H |
| 80 | 2 | — | piperazine-(4-CF3-pyrimidin-2-yl) | C(O)-phenyl-O-phenyl | H |
| 81 | 2 | — | 1-(4-fluorophenyl)-1-hydroxycyclohexyl | C(O)-phenyl-O-phenyl | H |
| 82 | 5 | — | HN-(4-bromophenyl) | C(O)-phenyl-O-phenyl | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

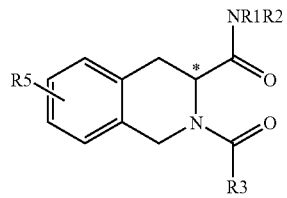

IIIa

| Compound # | Method | *R/S | R1NR2 | C(O)R3 | R5 |
|---|---|---|---|---|---|
| 83 | 5 | — | HN—(3-ethoxyphenyl) | C(O)—(3-phenoxyphenyl) | H |
| 84 | 5 | — | HN—(4-propylphenyl) | C(O)—(3-phenoxyphenyl) | H |
| 85 | 5 | — | HN—(4-(N-methylacetamido)phenyl) | C(O)—(3-phenoxyphenyl) | H |
| 86 | 3 | S | HN—(4-(N-methylacetamido)phenyl) | C(O)—(3-phenoxyphenyl) | H |
| 87 | 5 | — | HN—(4-butylphenyl) | C(O)—(3-phenoxyphenyl) | H |
| 88 | 3 | S | HN—(4-pentylphenyl) | C(O)—(3-phenoxyphenyl) | H |
| 89 | 5 | — | HN—(4-pentylphenyl) | C(O)—(3-phenoxyphenyl) | H |
| 90 | 7, 5 | — | HN—(4-(N-pentylacetamido)phenyl) | C(O)—(3-phenoxyphenyl) | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

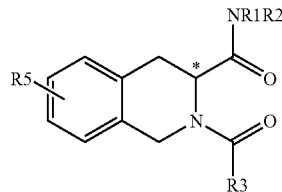

IIIa

| Compound # | Method | *R/S | R1NR2 | C(O)R3 | R5 |
|---|---|---|---|---|---|
| 91 | 7, 3 | S | HN–C6H4–N(Ac)(pentyl) | C(O)-3-phenoxyphenyl | H |
| 92 | 5 | — | HN–C6H4–F (4-F) | C(O)-3-phenoxyphenyl | H |
| 93 | 5 | — | HN–C6H4–I (4-I) | C(O)-3-phenoxyphenyl | H |
| 94 | 5 | — | HN–C6H4–hexyl (4-) | C(O)-3-phenoxyphenyl | H |
| 95 | 8, 5 | — | HN–C6H4–N(Me)C(O)propyl | C(O)-3-phenoxyphenyl | H |
| 96 | 5 | — | HN–C6H4–OEt (4-) | C(O)-3-phenoxyphenyl | H |
| 97 | 5 | — | HN-(6-chloropyridin-3-yl) | C(O)-3-phenoxyphenyl | H |
| 98 | 5 | — | HN-(pyridin-3-yl) | C(O)-3-phenoxyphenyl | H |
| 99 | 5 | — | HN-(6-methoxypyridin-3-yl) | C(O)-3-phenoxyphenyl | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 100 | 5 | — | HN-thiazol-2-yl | C(O)-3-phenoxyphenyl | H |
| 101 | 5 | — | HN-(4-butoxyphenyl) | C(O)-3-phenoxyphenyl | H |
| 102 | 7, 5 | — | HN-(4-(N-butylacetamido)phenyl) | C(O)-3-phenoxyphenyl | H |
| 103 | 7, 3 | S | HN-(4-(N-butylacetamido)phenyl) | C(O)-3-phenoxyphenyl | H |
| 104 | 7, 5 | — | HN-(4-(N-pentylacetamido)phenyl) | C(O)-3-phenoxyphenyl | H |
| 105 | 7, 3 | S | HN-(4-(N-pentylacetamido)phenyl) | C(O)-3-phenoxyphenyl | H |
| 106 | 3 | — | HN-(4-(3-methylbutyl)phenyl) | C(O)-3-phenoxyphenyl | H |
| 107 | 3 | S | HN-(6-pentylpyridin-3-yl) | C(O)-3-phenoxyphenyl | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 108 | 3 | — | HN—(5-pyridyl)-6-Cl | C(O)—phenyl(3-OPh, 4-OMe) | H |
| 109 | 10, 3 | S | HN—C6H4—4-F | C(O)—(2-pyridyl)-4-O-cyclohexyl | H |
| 110 | 10, 3 | S | HN—(5-pyridyl)-6-OMe | C(O)—(2-pyridyl)-4-O-cyclohexyl | H |
| 111 | 10, 3 | S | HN—C6H4—3-OEt | C(O)—(2-pyridyl)-4-O-cyclohexyl | H |
| 112 | 3 | S | HN—C6H4—4-butyl | C(O)—phenyl(3-O-(4-methoxyphenyl)) | H |
| 113 | 3 | — | HN—C6H4—4-butyl | C(O)—phenyl(3-OCH2Ph) | H |
| 114 | 3 | S | HN—C6H4—4-butyl | C(O)—phenyl(3-OCH2Ph) | H |
| 115 | 9, 6 | S | HN—C6H4—4-butyl | C(O)—phenyl(3-OPh, 4-OMe) | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 116 | 6 | S | HN-C6H4-(CH2)4- | C(O)-phenyl(OBn)(OMe) | H |
| 117 | 6 | S | HN-C6H4-(CH2)4- | C(O)-phenyl-O-cyclohexyl | H |
| 118 | 10, 6 | S | HN-C6H4-(CH2)4- | C(O)-pyridyl-O-phenyl | H |
| 119 | 10, 6 | S | HN-C6H4-(CH2)4- | C(O)-pyridyl-O-cyclohexyl | H |
| 120 | 6 | S | HN-C6H4-(CH2)4- | C(O)-phenyl-O-cyclopentyl | H |
| 121 | 13, 6 | S | HN-C6H4-(CH2)4- | C(O)-phenyl(OPh)(OEt) | H |
| 122 | 6 | S | HN-C6H4-(CH2)4- | C(O)-phenyl-O-tBu | H |
| 123 | 6 | S | HN-C6H4-(CH2)4- | C(O)-phenyl-CH2-morpholine | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

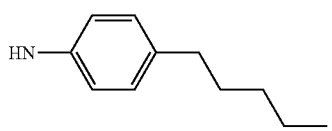

IIIa

| Compound # | Method | *R/S | R1NR2 | C(O)R3 | R5 |
|---|---|---|---|---|---|
| 124 | 6 | S | 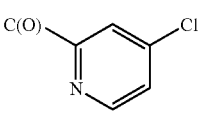 | 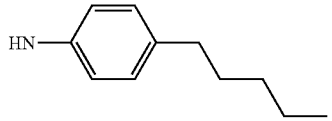 | H |
| 125 | 10, 6 | S | 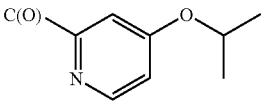 | 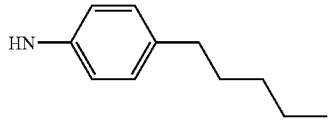 | H |
| 126 | 6 | S | 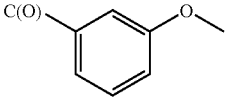 | 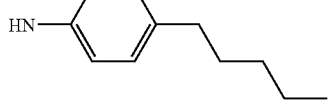 | H |
| 127 | 6 | S | 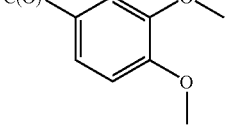 | 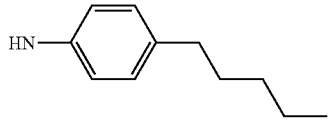 | H |
| 128 | 14, 6 | S | 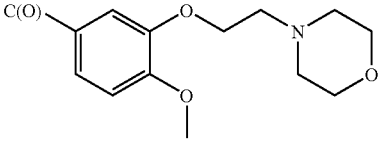 | 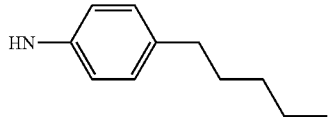 | H |
| 129 | 6 | S | 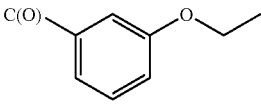 | 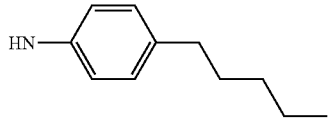 | H |
| 130 | 6 | S | 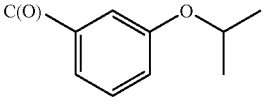 | 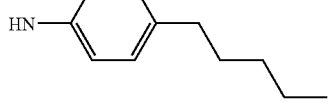 | H |
| 131 | 11, 6 | S | 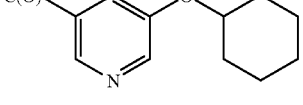 | | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 132 | 6 | S | HN-C6H4-(CH2)3-CH3 | C(O)-phenyl-2,3-diCl | H |
| 133 | 6 | S | HN-C6H4-(CH2)3-CH3 | C(O)-phenyl-3,5-diCl | H |
| 134 | 6 | S | HN-C6H4-(CH2)3-CH3 | C(O)-phenyl-3-Cl | H |
| 135 | 6 | S | HN-C6H4-(CH2)3-CH3 | C(O)-benzodioxane | H |
| 136 | 12, 6 | S | HN-C6H4-(CH2)3-CH3 | C(O)-phenyl-3-OiPr-4-OMe | H |
| 137 | 14, 6 | S | HN-C6H4-(CH2)3-CH3 | C(O)-phenyl-3-OiPr-5-O(CH2)2-morpholine | H |
| 138 | 6 | S | HN-C6H4-(CH2)3-CH3 | C(O)-phenyl-3,4,5-triOMe | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

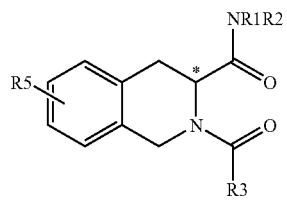

IIIa

| Compound # | Method | *R/S | R1NR2 | C(O)R3 | R5 |
|---|---|---|---|---|---|
| 139 | 12,6 | S | 4-pentylphenyl-NH | C(O)-phenyl-3-O-(S)-sec-butyl | H |
| 140 | 12,6 | S | 4-pentylphenyl-NH | C(O)-phenyl-3-O-(R)-sec-butyl | H |
| 141 | 12,6 | S | 4-pentylphenyl-NH | C(O)-phenyl-3-O-sec-butyl | H |
| 142 | 12,6 | S | 4-pentylphenyl-NH | C(O)-phenyl-3-O-isobutyl | H |
| 143 | 12,6 | S | 4-pentylphenyl-NH | C(O)-phenyl-3-O-isopropyl-4-methyl | H |
| 144 | 11,6 | S | 4-pentylphenyl-NH | C(O)-(5-isopropoxy-pyridin-3-yl) | H |
| 145 | 16,6 | S | 4-pentylphenyl-NH | C(O)-(5-isopropoxy-2-methoxy-pyridin-3-yl) | H |
| 146 | 17,6 | S | 4-pentylphenyl-NH | C(O)-(2-isopropoxy-pyridin-4-yl) | H |

TABLE 1-continued

Substituted 1,2,3,4-tetrahydroisoquinolines. Method column indicates synthetic method used to make the compound. Note that R1 is H except for compounds 80 and 81, where R1 and R2 form a cyclic amine. R5 is —H or an optional substituent. Compounds are racemic mixtures except where indicated. Compounds 18 and 19 are diastereomers (relative stereochemistry undetermined).

IIIa

| Compound # | Method | *R/S | R1NR2 | C(O)R3 | R5 |
|---|---|---|---|---|---|
| 147 | 10,6 | S | HN—⟨phenyl⟩—(CH₂)₄— | C(O)—(pyridyl-O-pyridyl) | H |

EXAMPLE 21

Disclosed Compounds Restore Chloride Ion Transport in Cells Expressing ΔF508 CFTR C127 cells are a murine mammary epithelial cell line obtained from ATCC (#CRL 1616, American Type Culture Collection, Manassas, Va.). C127 cells were transfected with a bovine papilloma virus-based eukaryotic expression vector containing genes for ΔF508 CFTR and neomycin resistance whose expression was driven by a metallothionein promoter. Clonal cell populations resistant to G418 and positive for staining with anti-CFTR antibody were identified.

C127 cells expressing ΔF508 CFTR were grown in microtiter plates in DMEM (Dulbecco's Modified Eagle Medium, Hyclone, Logan, Utah) supplemented with fetal bovine serum, antibiotics, and glutamine in a 37° C., 5% $CO_2$ atmosphere. Once confluent, the cells were loaded overnight with the disclosed compounds and a fluorescent dye sensitive to chloride ion concentration, N-(ethoxycarbonylmethyl)-6-methoxy quinolinium bromide (MQAE) (Verkman, Am. J. Physiol. 259 C375-C388 (1990)). MQAE was added to a concentration of 10 mM and compound mixtures were added to a total concentration of 12.5 µM.

The following day, cells were washed with chloride-containing buffer to remove extracellular MQAE and to quench intracellular MQAE fluorescence. Chloride buffer was flicked out and replaced with nitrate buffer with added forskolin and IBMX (isobutylmethylxanthine) to stimulate CFTR activity. Forskolin and IBMX increased and maintained intracellular cyclic AMP (cAMP) levels (cAMP is known to activate CFTR chloride channel activity). Buffers were adjusted to pH 7.4 and contained: 10 mM HEPES (N-2-Hydroxyethylpiperazine-N'-2-ethanesulfonic acid), 2.4 mM $K_2HPO_4$, 0.6 mM $KH_2PO_4$, 1.0 mM $CaSO_4$, 1.0 mM $MgSO_4$, 150 mM NaCl or $NaNO_3$, and 25 mM glucose.

The increase in MQAE fluorescence as a function of time was followed using 360 nm excitation and 460 nm emission wavelengths. Fluorescence increased as chloride flowed out of cells through CFTR and the rate of increase in fluorescence over the first five minutes was taken as a measure of chloride transport activity. The background activity of untreated ΔF508-expressing cells was low. Control wells treated with 5 mM 4-phenylbutyrate showed increased activity, as expected (Rubinstein et al., J. Clin. Invest. 100 2457-2465 (1997)). Separate control plates incubated at 28-30° C. and 5% $CO_2$ overnight also showed increased activity, consistent with the known effect of low temperature on CFTR trafficking (Denning et al., Nature 358 761-764 (1992)). In practice, chloride transport activity was scaled relative to untreated cells (0% activity) and low temperature-treated cells (100% activity).

Cells were treated with mixtures of up to 100 compounds per well for ca. 18 hours before the assay for chloride transport activity. Active mixtures, which caused the cells to have increased CFTR activity, were identified and their individual components tested to identify active single compounds. This process led to the identification of several diamides of tetrahydroisoquinoline as active compounds. Subsequently, the synthetic chemistry described in Examples 1-20 was used to generate the compounds in Table 2. Dose-response curves were generated and compounds were ranked based on their $EC_{50}$ values and maximal responses (the plateau level in activity at high compound concentration, as a percentage of the low temperature response). The $EC_{50}$ values and maximal response, or maximal response at a limiting concentration of 1.25 µM are shown in Table 2.

TABLE 2

| Compound # | % Maximal Response @ 1.25 µM | $EC_{50}$ (µM) | % of Maximal Response |
|---|---|---|---|
| 1 | — | 0.250 | 79 |
| 2 | — | 0.130 | 82 |
| 3 | — | 0.260 | 71 |
| 4 | — | 0.250 | 79 |
| 5 | — | 0.340 | 72 |
| 6 | — | 0.170 | 82 |
| 7 | — | 0.250 | 77 |
| 8 | — | 0.280 | 95 |
| 9 | — | 0.360 | 82 |
| 10 | — | 0.530 | 66 |
| 11 | — | 0.260 | 52 |
| 12 | — | 0.370 | 77 |

TABLE 2-continued

| Compound # | % Maximal Response @ 1.25 µM | $EC_{50}$ (µM) | % of Maximal Response |
|---|---|---|---|
| 13 | — | 0.300 | 60 |
| 14 | — | 0.220 | 85 |
| 15 | — | 0.330 | 64 |
| 16 | — | 0.240 | 71 |
| 17 | — | 0.067 | 65 |
| 18 | — | 0.087 | 59 |
| 19 | — | 0.150 | 69 |
| 20 | — | 1.24 | 28 |
| 21 | — | 0.170 | 28 |
| 22 | 36 | — | — |
| 23 | 34 | — | — |
| 24 | 32 | — | — |
| 25 | 61 | — | — |
| 26 | 33 | — | — |
| 27 | 44 | — | — |
| 28 | 32 | — | — |
| 29 | 39 | — | — |
| 30 | 34 | — | — |
| 31 | 30 | — | — |
| 32 | 48 | — | — |
| 33 | 30 | — | — |
| 34 | 36 | — | — |
| 35 | 36 | — | — |
| 36 | 38 | — | — |
| 37 | 32 | — | — |
| 38 | 47 | — | — |
| 39 | 41 | — | — |
| 40 | 34 | — | — |
| 41 | 34 | — | — |
| 42 | 63 | — | — |
| 43 | 56 | — | — |
| 44 | 44 | — | — |
| 45 | 67 | — | — |
| 46 | 65 | — | — |
| 47 | 46 | — | — |
| 48 | 39 | — | — |
| 49 | 48 | — | — |
| 50 | 40 | — | — |
| 51 | 55 | — | — |
| 52 | 40 | — | — |
| 53 | 61 | — | — |
| 54 | 30 | — | — |
| 55 | 63 | — | — |
| 56 | 53 | — | — |
| 57 | 30 | — | — |
| 58 | 45 | — | — |
| 59 | 45 | — | — |
| 60 | 35 | — | — |
| 61 | 44 | — | — |
| 62 | 32 | — | — |
| 63 | 34 | — | — |
| 64 | 34 | — | — |
| 65 | 56 | — | — |
| 66 | 45 | — | — |
| 67 | 85 | 0.270 | 70 |
| 68 | 34 | — | — |
| 69 | 43 | — | — |
| 70 | 33 | — | — |
| 71 | 33 | — | — |
| 72 | 33 | — | — |
| 73 | 34 | — | — |
| 74 | 31 | — | — |
| 75 | — | 0.270 | 82 |
| 76 | — | 0.400 | 36 |
| 77 | — | 0.350 | 30 |
| 78 | — | 0.250 | 40 |
| 79 | — | 0.230 | 73 |
| 80 | 31 | — | — |
| 81 | 37 | — | — |
| 82 | — | 0.260 | 77 |
| 83 | — | 0.280 | 79 |
| 84 | — | 0.200 | 76 |
| 85 | — | 0.096 | 74 |
| 86 | — | 0.066 | 54 |
| 87 | — | 0.069 | 74 |
| 88 | — | 0.020 | 76 |
| 89 | — | 0.100 | 87 |
| 90 | — | 0.059 | 66 |
| 91 | — | 0.029 | 70 |
| 92 | — | 0.210 | 72 |
| 93 | — | 0.290 | 60 |
| 94 | — | 0.290 | 77 |
| 95 | — | 0.150 | 80 |
| 96 | — | 0.420 | 33 |
| 97 | — | 0.110 | 60 |
| 98 | — | 0.310 | 55 |
| 99 | — | 0.270 | 70 |
| 100 | — | 0.430 | 59 |
| 101 | — | 0.120 | 66 |
| 102 | — | 0.140 | 70 |
| 103 | — | 0.052 | 76 |
| 104 | — | 0.077 | 93 |
| 105 | — | 0.038 | 86 |
| 106 | — | 0.130 | 84 |
| 107 | — | 0.049 | 54 |
| 108 | — | 0.100 | 60 |
| 109 | — | 0.096 | 87 |
| 110 | — | 0.400 | 64 |
| 111 | — | 0.150 | 73 |
| 112 | — | 0.039 | 71 |
| 113 | — | 0.069 | 91 |
| 114 | — | 0.059 | 72 |
| 115 | — | 0.012 | 74 |
| 116 | — | 0.018 | 88 |
| 117 | — | 0.019 | 72 |
| 118 | — | 0.016 | 79 |
| 119 | — | 0.0062 | 75 |
| 120 | — | 0.013 | 82 |
| 121 | — | 0.0063 | 80 |
| 122 | — | 0.010 | 83 |
| 123 | — | 0.095 | 63 |
| 124 | — | 0.069 | 60 |
| 125 | — | 0.0053 | 84 |
| 126 | — | 0.091 | 82 |
| 127 | — | 0.180 | 83 |
| 128 | — | 0.110 | 63 |
| 129 | — | 0.029 | 73 |
| 130 | — | 0.0056 | 81 |
| 131 | — | 0.055 | 89 |
| 132 | — | 0.097 | 47 |
| 133 | — | 0.014 | 70 |
| 134 | — | 0.053 | 51 |
| 135 | — | 0.290 | 56 |
| 136 | — | 0.0033 | 71 |
| 137 | — | 0.180 | 69 |
| 138 | — | 0.093 | 67 |
| 139 | — | 0.008 | 84 |
| 140 | — | 0.0044 | 84 |
| 141 | — | 0.012 | 84 |
| 142 | — | 0.008 | 88 |
| 143 | — | 0.0059 | 85 |
| 144 | — | 0.031 | 95 |
| 145 | — | 0.025 | 75 |
| 146 | — | 0.015 | 41 |
| 147 | — | 0.041 | 32 |

EXAMPLE 22

Disclosed Compounds Increase Chloride Ion Transport in a Variety of Cells Expressing Wild-type CFTR Wild-type CFTR is also known to have a trafficking defect that results in about 70% of expressed protein being degraded. The ΔF508 defect is much more severe, with only a few % of total protein escaping degradation. Because cell lines in which wild-type CFTR is expressed at measurable levels were readily available, they were used to test compounds for their ability to increase CFTR activity.

C127 cells stably transfected with wild-type CFTR were generated as described in Example 21. The effects of Compound 2, a prototype Tic diamide, were tested on C127 cells expressing wild-type CFTR using the screening assay format described in Example 21. FIG. 1A shows that chloride efflux rates were increased approximately two-fold. The chloride efflux rates in the presence (white circles) and absence of cAMP agonists (black circles) are shown as measured using MQAE. Since chloride transport was mediated exclusively by wild-type CFTR in these cells, this result demonstrates that Compound 2 was able to rescue the wild-type CFTR trafficking defect.

Compound 2 was also tested on three human cell lines known to express wild-type CFTR. These cell lines are more relevant to human therapy than the cell line used for screening in several respects: they are of human origin, CFTR is not overexpressed, and CFTR expression is controlled by the native promoter. Compound 2 increased cAMP-dependent chloride channel activity in the T84 human colon carcinoma line, the Calu-3 human lung adenocarcinoma line, and the Caco-2 human colorectal adenocarcinoma line (FIGS. 1-B,C, & D, white circles with cAMP, black circles without cAMP). These results are consistent with rescue of wild-type CFTR in these cells. However, because the measured chloride transport activity is the sum of the activities of a number of transporters including CFTR, these effects could in principle also arise from an effect on another chloride transporter.

EXAMPLE 23

Disclosed Compounds Restore Chloride Ion Conductance in Human Cystic Fibrosis Cells The CFT1 cell line, an airway epithelial cell line derived from a ΔF508 homozygote patient, is a realistic system for evaluating potential CF therapeutics (Yankaskas et al., Am. J. Physiol. 264 C1219-C1230 (1993)). In contrast to the C127 cell system used in the screen (murine cells, CFTR overexpressed), CFT1 cells express endogenous (low) levels of mutant CFTR in the context of a human airway epithelial cell.

The whole-cell patch clamp technique was used to measure the effect of Compound 125 on chloride conductance in the CFT1 cell line. In this measurement, a high-resistance seal was formed between a pipette and the plasma membrane of an isolated cell. The patch of membrane covered by the pipette was ruptured, giving electrical access to the interior of the cell. The aggregate conductance due to all of the ion transport processes across the plasma membrane was measured using electrodes in the bath and pipette. In the present case, the ionic composition of the bath and electrode solutions was adjusted so that only chloride transport would be measured. Forskolin was added to the bath solution to induce CFTR activity.

Membrane currents were recorded from single cells by using the whole-cell configuration of the patch-clamp technique. Cells were mounted on the stage of an inverted microscope, and whole cell currents were recorded with a I D amplifier (Axon Instruments, Union City, Calif.). Chloride currents were elicited by 400 ms voltage pulses from −100 to 100 mV in 20 mV increments every 5 sec. The amplitude of chloride currents was measured at the 200 ms time point of each trace. Pclamp 8.02 software (Axon) was used for pulse generation, data acquisition through a Digidata 1320 (Axon), and analysis.

Whole-cell chloride currents were recorded by using an extracellular solution contained: 140 mM N-methyl-D-glucamine (NMG) chloride, 4 mM CsCl, 0.1 mM $CdCl_2$, 10 mM HEPES, 10 mM glucose, 1 mM $MgCl_2$, 2 mM $CaCl_2$, with the pH at 7.4. The standard intracellular solution contained: 130 mM CsCl, 20 mM tetraethylammonium chloride, 10 mM HEPES, 10 mM EGTA (Ethylenebis (oxyethylenenitrilo)] tetraacetic acid), 10 mM Mg-ATP, 0.1 mM Li GTP, at a pH of 7.4. During an experiment a culture dish was continuously perfused with Tyrode's solution which contained (in mM): 137 mM NaCl, 5 mM KCl, 1 mM $MgCl_2$, 1.8 mM $CaCl_2$, 10 mM HEPES, 10 mM glucose, at a pH of 7.4. After forming whole-cell configuration the cell was perfused with the NMG solution via a rapid perfusion system.

Figure 2:
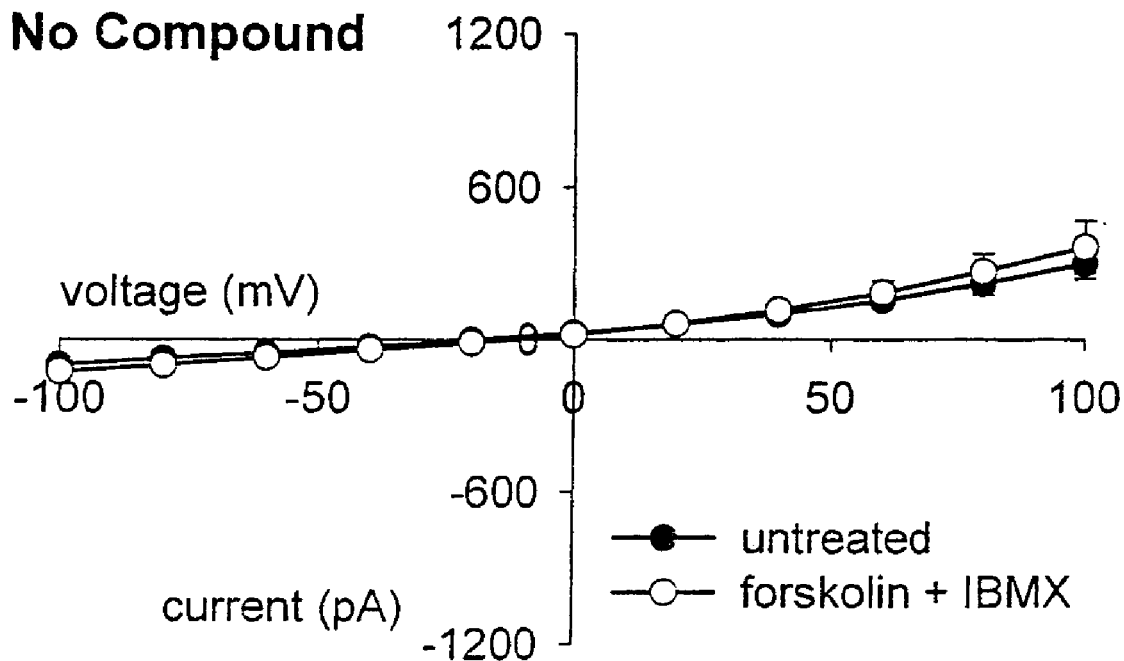
FIG. 2 is a pair of graphs showing voltage vs. current plots from whole-cell patch clamp electrophysiology in the presence and absence of cAMP agonists for untreated CFT1 cells and CFT1 cells treated with 10 μM Compound 125 for 24 to 48 hours. Points marked with asterisks differ significantly from controls in the absence of cAMP agonists: *, P<0.05; **, P<0.01.
Figure 2:
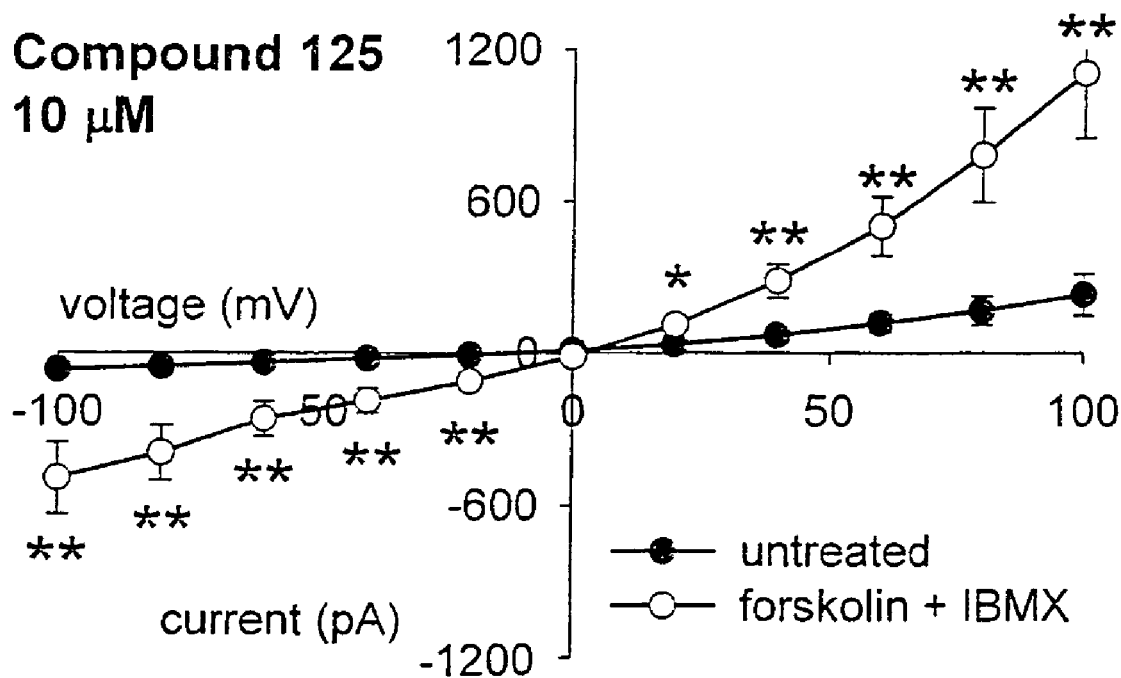
Figure 3:
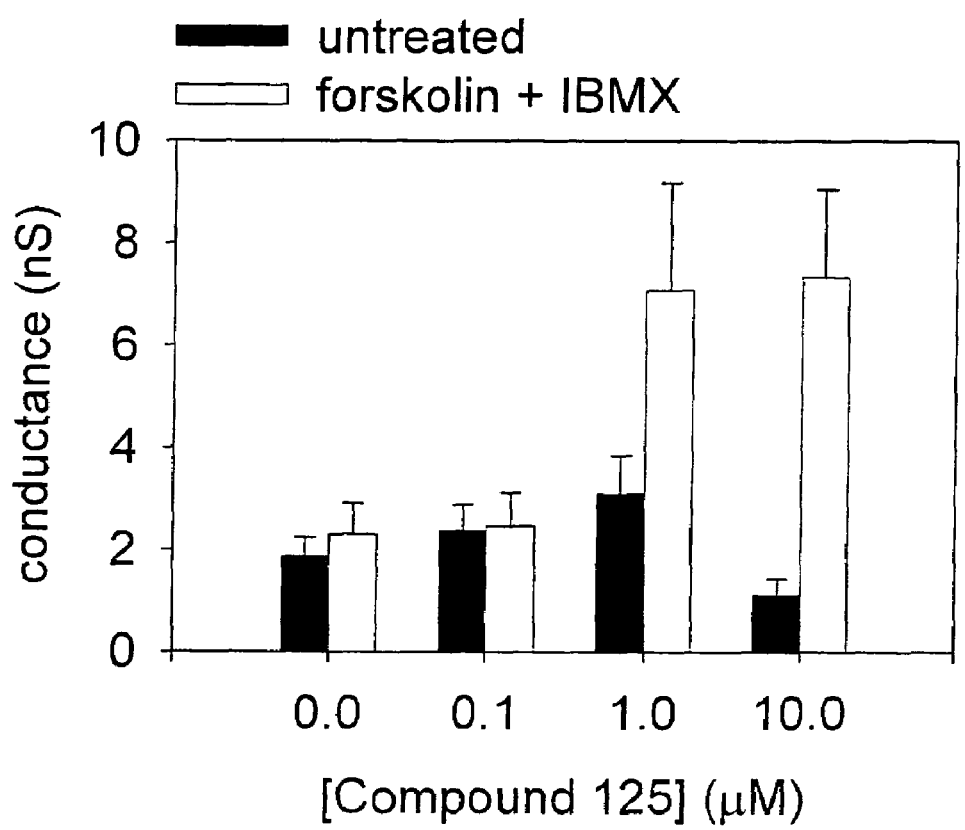
FIG. 3 is a graph demonstrating that Compound 125 increases chloride ion conductance in CFT1 cells, which express ΔF508 CFTR. Chloride conductances on the presence and absence of cAMP agonists for CFT1 cells treated with different concentrations of Compound 125 are shown.
Figure 4:
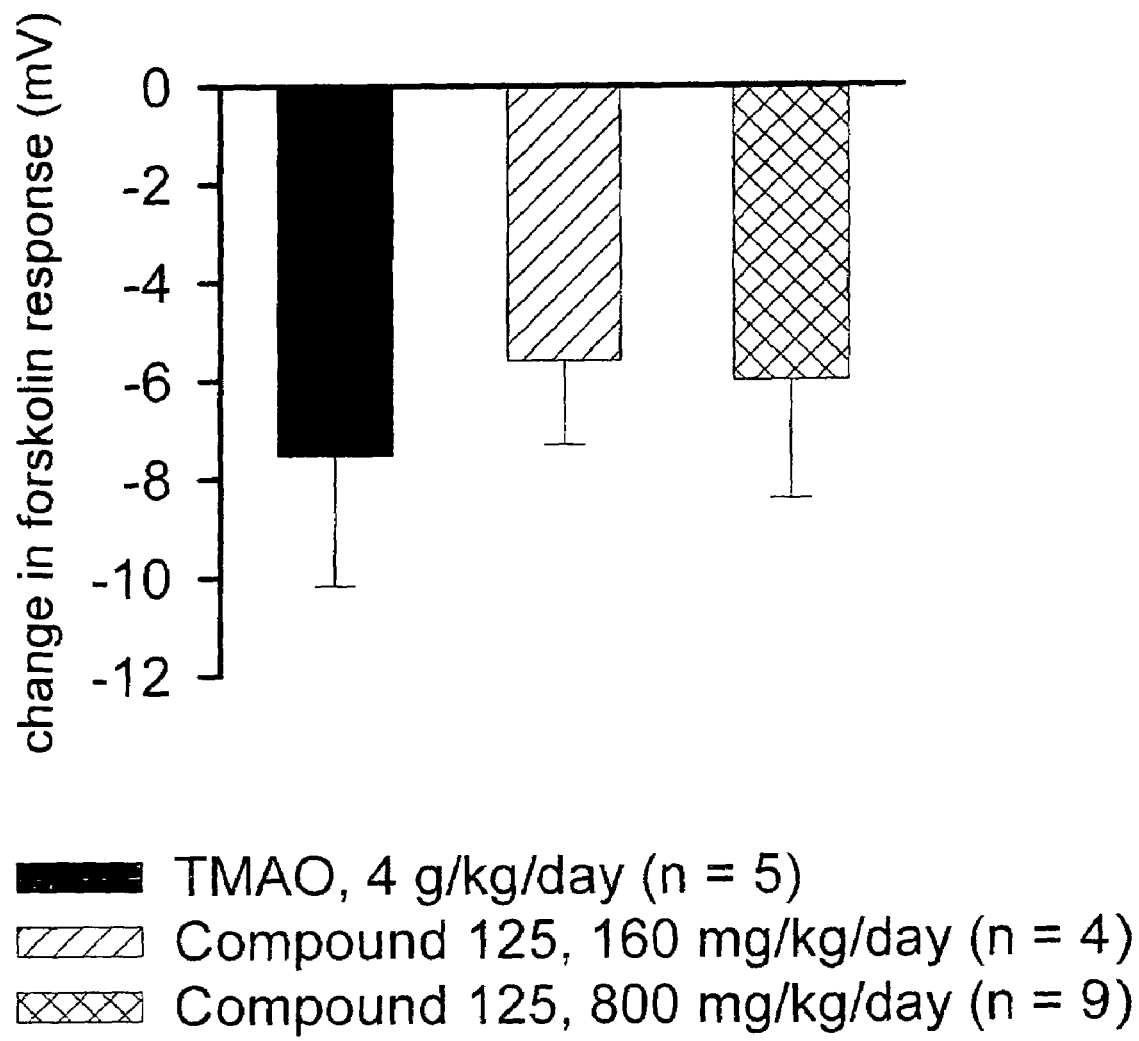
FIG. 4 is a chart showing that Compound 125 increases chloride ion transport in vivo as demonstrated in rectal potential difference measurements in female wild-type mice.

FIG. 2 shows voltage vs. current plots in the presence and absence of cAMP agollists for untreated CFT1 cells and CFT1 cells treated with 10 μM Compound 125 for 24 to 48 hours. The response to forskolin was dramatically increased, consistent with restoration of CFTR function. FIG. 3 summarizes the chloride conductances (slopes of the voltage vs. current plots) measured in CFT1 cells treated with 0, 0.1, 1, and 10 μM of Compound 125. After 24 to 48 h, Compound 125 dramatically increased the measured chloride conductance after forskolin treatment, but had little or no effect in the absence of forskolin, consistent with rescue of ΔF508 CFTR. Thus, Compound 125 restored relevant chloride transport activity in a cell line derived from human CF airway epithelium.

EXAMPLE 24

Disclosed Compounds Increase Chloride Ion Transport in Wild-type Mice

Compounds were tested in normal mice because it has been shown using rectal potential difference (RPD) measurements that the chemical chaperone trimethylamine oxide (TMAO) increased CFTR activity in both wild-type and ΔF508 CFTR transgenic mice, presumably by assisting CFTR folding (Fischer et al., Am. J. Physiol. Lung Cell. Mol. Physiol. 281 L52-L57 (2001)). TMAO is known to restore proper folding of ΔF508 CFTR and other misfolded proteins. Since the disclosed compounds were shown to increase activity in cells expressing wild-type CFTR, it was reasonable to test for an effect in wild-type mice.

In the rectal PD measurement, solutions of electrolyte were allowed to flow over epithelial tissue near a sensing electrode. The potential difference between the sensing electrode and a subcutaneous reference electrode was measured for electrolyte solutions without and with added forskolin. Measurements were performed as described in Fischer et al., Am. J. Physiol. Lung Cell. Mol. Physiol. 281 L52-L57 (2001). Measurements were done in presence of: 100 μM amiloride (to block $Na^+$ absorption), 2 mM Ba acetate (to block $K^+$ secretion), and in chloride-free solutions (to generate a driving force for chloride secretion). Under these conditions, the perfusion of forskolin into the lumen of the rectum caused a hyperpolarization of the RPD (i.e., movement to more negative values). The measured forskolin-stimulated RPD is likely a measure of CFTR activity because 1) it is stimulated by forskolin, 2) it is driven by the chloride gradient and, and 3) the other major ion conductances that contribute to the rectal PD ($Na^+$, $K^+$) are blocked. Consistent with this assertion, no forskolin response was seen in RPD measurements on transgenic ΔF508 CFTR mice, which lack functional CFTR.

Compound 125 was dissolved in sesame oil and administered to 6 wild-type C57black6/J mice 5-8 weeks old by intraperitoneal injection twice a day for three days. A net dose of 160 mg/kg/day was given and RPD measurements were performed ca. 6 h after the last dose. Compound 125 had no effect on the two male mice in the group, but significantly increased the forskolin response in RPD measurements by 5.6 mV (P=0.012 ) relative to vehicle in the 4 female mice. i.e., the forskolin response (RPD after forskolin minus RPD before forskolin) was larger in compound-treated mice than in vehicle-treated mice by 5.6 mV.

In a confirmatory study, 6 male and 9 female mice were dosed with Compound 125 at 800 mg4(g/day by intraperitoneal injection. Sesame oil vehicle was administered to separate groups of 6 male and 9 female mice. In female mice, the forskolin response for Compound 125 was increased by 6.0 mV relative to vehicle-treated mice (p=0.026). There was again no effect of compound in male mice.

The increase in cAMP-dependent chloride transport in female wild-type mice is consistent with an increase in CFTR activity resulting from treatment with Compound 125. The effect was similar in magnitude to the effect previously measured for the chemical chaperone trimethylamine oxide, which increased the forskolin response in female wild-type mice by 7.5 mV (4 g/kg/day dose for 2 days) FIG. 3 shows the effect (corrected for vehicle) of TMAO (black bar) versus Compound 125 at 160 mg/kg/day (diagonal hatched bar) and 800 mg/kg/day (crosshatched bar). Equivalent effects were seen with 160 mg/kg/day and 800 mg/kg/day Compound 125, which may reflect a plateau in the uptake of the compound from sesame oil vehicle in the peritoneal cavity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by structural formula Ib:

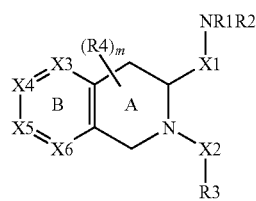

wherein:

X1 and X2 are independently —C(O)— or —S(O)—;
X3, X4, X5, and X6 are —CH—;
Ring B is optionally substituted at any substitutable carbon;
m is 0, 1 or 2;
each R4 is independently halogen, —OH, —SH, —R$^a$, —OR$^a$, —SR$^a$, —NH$_2$, —NHR$^a$, —NR$^a{}_2$, —C(O)NR$^a{}_2$, —CF$_3$, —CN, or —NO$_2$; and
i) R1 is —H;
R2 is —X7-R6, wherein
X7 is a covalent bond, a C5-C12 linear or branched aliphatic group containing 1, 2, or 3 double bonds, or a C1-C12 alkyl chain optionally interrupted by —O— or —S—;
R6 is —SH, diphenylmethylene, or a 5 or 6 membered aryl, heteroaryl, heterocyclic or monocyclic C4-C6 cycloalkyl group;
each cyclic group represented by R6 is optionally substituted with one or more groups selected from C4-C6 cycloalkyl, halogen, —CF$_3$, —R$^d$, —OR$^d$, —SR$^d$, —COR$^d$, —OH, —SH, phenyl, phenoxyl, benzyl, benzoyl, N-morpholinyl, —NR$^d{}_2$, —NR$^d$COR$^e$, N-aniline, —NO$_2$, and —CN;

or, R1 and R2, taken together with the nitrogen to which they are bonded, are an optionally substituted 6-membered heterocyclic group; and R3 is a six-membered aryl or heteroaryl group that is substituted or is fused to another ring; or ii) R1 and R2 are independently —H or an optionally substituted aliphatic, aryl, heteroaryl, heterocyclic, or monocyclic cycloalkyl group, provided that R1 and R2 are not both —H;

or, R1 and R2, taken together with the nitrogen to which they are bonded, are an optionally substituted heterocyclic group; and R3 is an optionally substituted 2-naphthyl, 6-(1,4 benzodioxan)yl, 6-indolyl, or 2-(9-fluorenon)yl group, or a phenyl or pyridyl group substituted with one or more groups selected from halogen, —CF$_3$, —NO$_2$, —CN, —R$^c$, —OR$^c$, and —XR$^f$;

wherein optional substituents on the aliphatic group are, independently, —OH, halogen (—Br, —Cl, —I and —F), —R, —OR, —CH$_2$R, —CH$_2$CH$_2$R, —OCH$_2$R, —CH$_2$OR, —CH$_2$CH$_2$OR, —CH$_2$OC(O)R, —O—COR, —COR, —SR, —SCH$_2$R, —CH$_2$SR, —SOR, —SO$_2$R, —CN, —NO$_2$, —COOH, —SO$_3$H, —COOR, —CHO, —CONH$_2$, —CONHR, —CON(R)$_2$, —NHCOR, —NRCOR, —NHCONH$_2$, —NHCONRH, —NHCON(R)$_2$, —NRCONH$_2$, —NRCONRH, —NRCON(R)$_2$, —C(=NH)—NH$_2$, —C(=NH)—NHR, —C(=NH)—N(R)$_2$, —C(=NR)—NH$_2$, —C(=NR)—NHR, —C(=NR)—N(R)$_2$, —SO$_2$NH$_2$, —SO$_2$NHR, —SO$_2$NR$_2$, —SH, and —SO$_k$R (k is 0, 1 or 2); each R being, independently, an unsubstituted alkyl, cycloalkyl, benzyl, aryl, or heteroaryl group;

wherein

X is —O—, —S—, —C(O)—, —S(O)—, —CH$_2$—, —CH$_2$CH$_2$—, —OCH$_2$—, —OCH$_2$CH$_2$—, —SCH$_2$—, or —SCH$_2$CH$_2$—;

each R$^a$ and R$^c$ is independently a C1-C5 branched or linear alkyl group;

each R$^d$ and R$^e$ is independently a C1-C7 branched or linear alkyl group; and R$^f$ is an optionally substituted phenyl, pyridyl, N-pyridyl, N-morpholinyl, furanyl, thienyl, isoxazolyl, imidazolyl, pyrazolyl, pyrrolyl, pyrrolidyl, piperidyl, piperazyl, benzofuranyl, tetrazolyl, thiazolyl, tetrazolyl, benzothiazolyl, benzimidazolyl cyclobutyl, cyclopentyl, or cyclohexyl group.

2. The compound of claim 1, wherein

Ring B is substituted at any substitutable carbon with zero, one, or more groups R5 independently selected from halogen, —OH, —SH, —R$^b$, —OR$^b$, —SR$^b$, —NH$_2$, —NHR$^b$, —NR$^b{}_2$, —C(O)NR$^b{}_2$, —CF$_3$, —CN, and —NO$_2$; and wherein each R$^b$ is independently a C1-C5 branched or linear alkyl group.

3. The compound of claim 2, wherein X1 and X2 are —C(O)—.

4. The compound of claim 3, wherein the compound is represented by structural formula III:

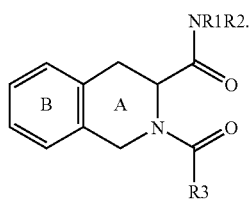

5. The compound of claim 4, wherein
R1 is —H;
R2 is —X7-R6, wherein
X7 is a covalent bond or a C1-C12 alkyl chain optionally interrupted by —O— or —S—;
R6 is —SH, diphenylmethylene, or a 5 or 6 membered aryl, heteroaryl, heterocyclic or monocyclic C4-C6 cycloalkyl group;
each cyclic group represented by R6 is optionally substituted with one or more groups selected from C4-C6 cycloalkyl, halogen, —$CF_3$, $R^d$, —$OR^d$, —$SR^d$, —$COR^d$, —OH, —SH, phenyl, phenoxyl, benzyl, benzoyl, N-morpholinyl, —$NR^d_2$, —$NR^d COR^e$, N-aniline, —$NO_2$, and —CN; and
R3 is a six-membered aryl or heteroaryl group that is substituted or is fused to another ring.

6. The compound of claim 4, wherein
R1 and R2 are independently —H or an optionally substituted aliphatic, aryl, heteroaryl, heterocyclic, or monocyclic cycloalkyl group, provided that R1 and R2 are not both —H;
or, R1 and R2, taken together with the nitrogen to which they are bonded, are an optionally substituted heterocyclic group; and
R3 is an optionally substituted 2-naphthyl, 6-(1,4 benzodioxan)yl, 6-indolyl, or 2-(9-fluorenon)yl group, or a phenyl or pyridyl group substituted with one or more groups selected from halogen, —$CF_3$, —$NO_2$, —CN, —$R^c$, —$OR^c$, and —$XR^f$.

7. The compound of claim 6, wherein the group represented by $R^f$ is optionally substituted with one or more groups selected from halogen, —$CF_3$, —$NO_2$, —CN, —$R^c$, and —$OR^c$.

8. The compound of claim 7, wherein R3 is a substituted phenyl or pyridyl group.

9. The compound of claim 5, wherein
R1 is H;
R2 is —X7-R6, wherein
X7 is a covalent bond or a C1-C4 alkyl chain optionally interrupted by —O— or —S—;
R6 is —SH, diphenylmethylene, or a phenyl, naplithyl, 3-quinolinyl, 6-quinolinyl, 2-thiazolyl, 2-furanyl, 5-indanyl, 2-(1,8-benzodiazin)yl, 6-(1,4-benzodioxan)yl, 5-(1,3-benzodioxol)yl, 5-benzimidazolyl, 3-pyridyl, or C4-C6 cycloalkyl group; and
wherein the cyclic groups represented by R6 are optionally substituted with one or more groups selected from halogen, —$CF_3$, —$R^d$, —$OR^d$, —$SR^d$, —$COR^d$, —OH, —SH, phenyl, phenoxyl, benzyl, benzoyl, N-morpholine, —$NR^d_2$, —$NR^d COR^e$, N-aniline, —$NO_2$, —CN, and C4-C6 cycloalkyl.

10. The compound of claim 4, wherein the compound is represented by structural formula IV:

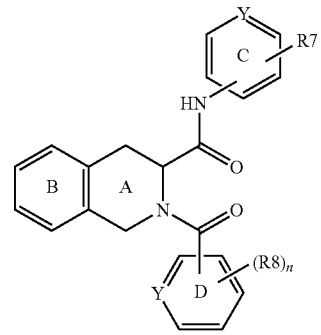

wherein
each Y is independently —N— or —CH—;
R7 is halogen, —$CF_3$, —$R^g$, —$OR^g$, —$SR^g$, —$COR^g$, —OH, —SH, phenyl, phenoxyl, benzyl, benzoyl, N-morpholinyl, —$NR^g_2$, —$NR^g COR^h$, N-aniline, —$NO_2$, —CN, or C4-C6 cycloalkyl;
each R8 is halogen, —$CF_3$, —$NO_2$, —CN, —$R^i$, —$OR^i$, or an optionally substituted phenoxy, phenyl sulfide, phenylsulfonyl, benzyl sulfide, benzyl, benzyloxy, benzoyl, —O-pyridyl, —$CH_2$—N-morpholine, —$OCH_2CH_2$—N-morpholine, cyclohexyloxy, or cyclopentyloxy group; and
n is 1 or 2; and
wherein $R^g$, $R^h$, and $R^i$ are each independently a C1-C8 branched or linear alkyl group.

11. The compound of claim 10, wherein the compound is represented by structural formula V:

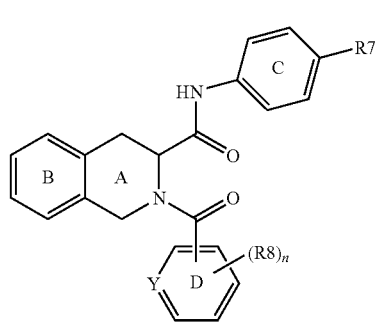

wherein
Y is —N— or —CH—;
R7 is —$R^j$, —$NR^j(CO)R^k$, or halogen;
each R8 is independently phenoxy, benzyloxy, C4-C6 cycloalkoxy, halogen, methoxy, ethoxy, 2-propyloxy, tert-butyloxy, 2-butyloxy, 3-pentyloxy, or methyl;
wherein $R^j$ is a C4-C8 linear alkyl group and $R^k$ is a C1-C4 branched or linear alkyl group.

12. A compound represented by structural formula VI:

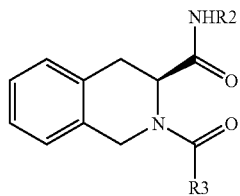   VI wherein
i) R3 is represented by structural formula R3$^a$:

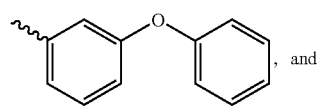   R3$^a$, and

R2 is represented by one of structural formulas R2$^a$ to R2$^c$:

   R2$^a$

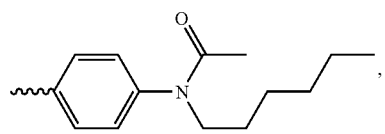   R2$^b$

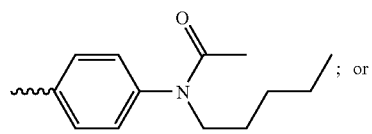   R2$^c$ ; or ii) R2 is represented by structural formula R2$^d$:

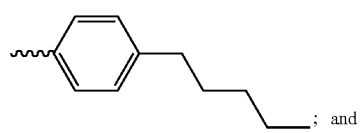   R2$^d$ ; and

R3 is represented by one of structural formulas R3$^a$ or R3$^b$ to R3$^v$:

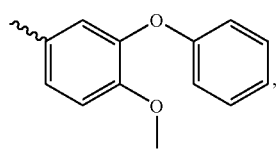   R3$^b$,

-continued

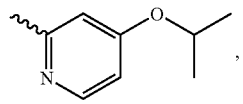   R3$^c$,

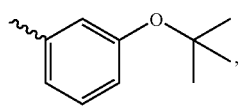   R3$^d$,

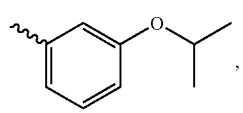   R3$^e$,

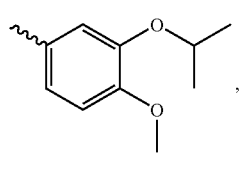   R3$^f$,

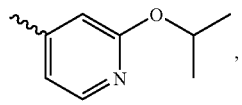   R3$^g$,

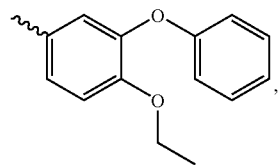   R3$^h$,

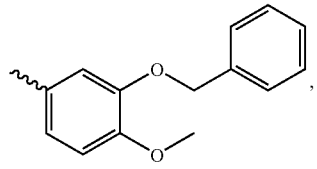   R3$^i$,

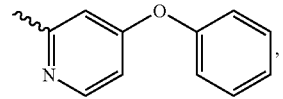   R3$^j$,

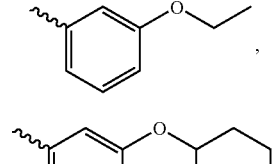   R3$^k$,

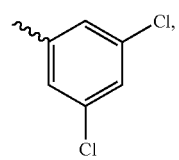   R3$^l$,

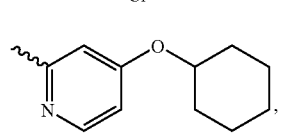   R3$^m$,

R3$^n$

13. The compound of claim 12, wherein R2 is represented by structural formula R2$^a$ and R3 is represented by structural formula R3$^a$.

14. The compound of claim 12, wherein

R2 is represented by structural formula R2$^d$; and

R3 is represented by one of structural formulas R3$^a$ to R3$^g$.

15. A method of improving mucociliary clearance in a subject affected by chronic obstructive pulmonary disease, emphysema, asthma or bronchitis, comprising the step of administering to the subject an effective amount of a compound represented by structural formula VI:

or a pharmaceutically acceptable salt thereon wherein i) R3 is represented by structural formula R3$^a$:

R2 is represented by one of structural formulas R2$^a$ to R2$^c$:

ii) R2 is represented by structural formula R2$^d$:

R3 is represented by one of structural formulas R3$^a$ or R3$^b$ to R3$^v$:

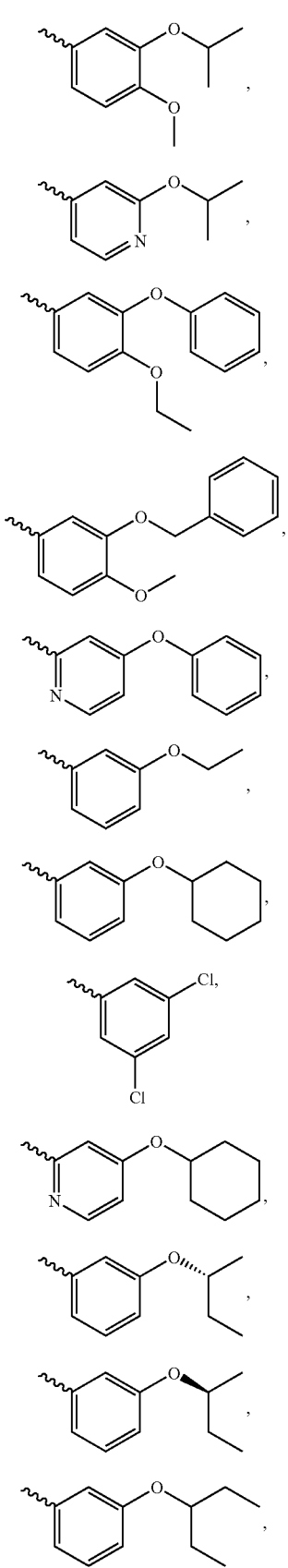

R3<sup>f</sup>, R3<sup>g</sup>, R3<sup>h</sup>, R3<sup>i</sup>, R3<sup>j</sup>, R3<sup>k</sup>, R3<sup>l</sup>, R3<sup>m</sup>, R3<sup>n</sup>, R3<sup>o</sup>, R3<sup>p</sup>, R3<sup>q</sup>

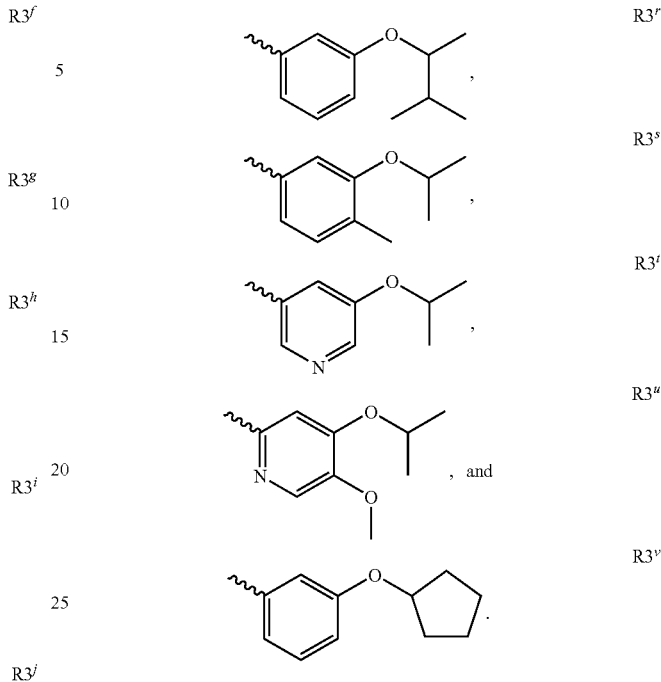

R3<sup>r</sup>, R3<sup>s</sup>, R3<sup>t</sup>, R3<sup>u</sup>, and R3<sup>v</sup>.

16. The method of claim 15, wherein R2 is represented by structural formula R2$^a$ and R3 is represented by structural formula R3$^a$.

17. The method of claim 16, wherein
R2 is represented by structural formula R2$^d$; and
R3 is represented by one of structural formulas R3$^a$ to R3$^g$.

18. A method of treating cystic fibrosis in a human in need of such treatment carrying the homozygous ΔF 508-CFTR mutation, comprising the step of administering to the subject an effective amount of a compound represented by structural formula Ib:

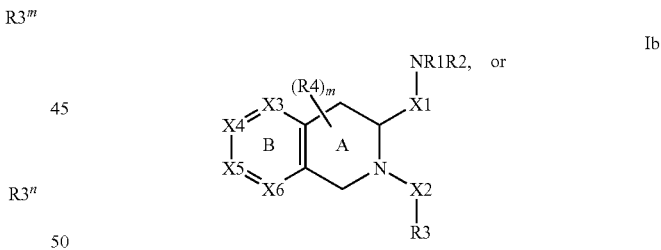

a pharmaceutically acceptable salt thereof wherein:
X1 and X2 are independently —C(O)— or —S(O)—;
X3, X4, X5, and X6 are —CH—;
Ring B is optionally substituted at any substitutable carbon;
m is 0, 1 or 2;
each R4 is independently halogen, —OH, —SH, —R$^a$, —OR$^a$, —SR$^a$, —NH$_2$, —NHR$^a$, —NR$^a{}_2$, —C(O)NR$^a{}_2$, —CF$_3$, —CN, or —NO$_2$; and
i) R1 is —H;
R2 is —X7-R6, wherein
X7 is a covalent bond, a C5-C12 linear or branched aliphatic group containing 1, 2, or 3 double bonds, or a C1-C12 alkyl chain optionally interrupted by —O— or —S—;

R6 is —SH, diphenylmethylene, or a 5 or 6 membered aryl, heteroaryl, heterocyclic or monocyclic C4-C6 cycloalkyl group;

each cyclic group represented by R6 is optionally substituted with one or more groups selected from C4-C6 cycloalkyl, halogen, —CF$_3$, —R$^d$, —OR$^d$, —SR$^d$, —COR$^d$, —OH, —SH, phenyl, phenoxyl, benzyl, benzoyl, N-morpholinyl, —NR$^d{}_2$, —NR$^d$COR$^e$, N-aniline, —NO$_2$, and —CN;

or, R1 and R2, taken together with the nitrogen to which they are bonded, are an optionally substituted 6-membered heterocyclic group; and R3 is a six-membered aryl or heteroaryl group that is substituted or is fused to another ring; or ii) R1 and R2 are independently —H or an optionally substituted aliphatic, aryl, heteroaryl, heterocyclic, or monocyclic cycloalkyl group, provided that R1 and R2 are not both —H;

or, R1 and R2, taken together with the nitrogen to which they are bonded, are an optionally substituted heterocyclic group; and R3 is an optionally substituted 2-naphthyl, 6-(1,4 benzodioxan)yl, 6-indolyl, or 2-(9-fluorenon)yl group, or a phenyl or pyridyl group substituted with one or more groups selected from halogen, —CF$_3$, —NO$_2$, —CN, —R$^c$, —OR$^c$, and —XR$^f$;

wherein optional substituents on the aliphatic group are, independently, —OH, halogen (—Br, —Cl, —I and —F), —R, —OR, —CH$_2$R, —CH$_2$CH$_2$R, —OCH$_2$R, —CH$_2$OR, —CH$_2$CH$_2$OR, —CH$_2$OC(O)R, —O—COR, —COR, —SR, —SCH$_2$R, —CH$_2$SR, —SOR, —SO$_2$R, —CN, —NO$_2$, —COOH, —SO$_3$H, —COOR, —CHO, —CONH$_2$, —CONHR, —CON(R)$_2$, —NHCOR, —NRCOR, —NHCONH$_2$, —NHCONRH, —NHCON(R)$_2$, —NRCONH$_2$, —NRCONRH, —NRCON(R)$_2$, —C(=NH)—NH$_2$, —C(=NH)—NHR, —C(=NH)—N(R)$_2$, —C(=NR)—NH$_2$, —C(=NR)—NHR, —C(=NR)—N(R)$_2$, —SO$_2$NH$_2$, —SO$_2$NHR, —SO$_2$NR$_2$, —SH, and —SO$_k$R (k is 0, 1 or 2); each R being, independently, an unsubstituted alkyl, cycloalkyl, benzyl, aryl, or heteroaryl group;

wherein
X is —O—, —S—, —C(O)—, —S(O)—, —CH$_2$—, —CH$_2$CH$_2$—, —OCH$_2$—, —OCH$_2$CH$_2$—, —SCH$_2$—, or —SCH$_2$CH$_2$—;

each R$^a$ and R$^c$ is independently a C1-C5 branched or linear alkyl group;

each R$^d$ and R$^e$ is independently a C1-C7 branched or linear alkyl group; and R$^f$ is an optionally substituted phenyl, pyridyl, N-pyridyl, N-morpholinyl, furanyl, thienyl, isoxazolyl, imidazolyl, pyrazolyl, pyrrolyl, pyrrolidyl, piperidyl, piperazyl, benzofuranyl, tetrazolyl, thiazolyl, tetrazolyl, benzothiazolyl, benzimidazolyl cyclobutyl, cyclopentyl, or cyclohexyl group.

19. The method of claim 18, wherein

Ring B is substituted at any substitutable carbon with zero, one, or more groups R5 independently selected from halogen, —OH, —SH, —R$^b$, —OR$^b$, —SR$^b$, —NH$_2$, —NHR$^b$, —NR$^b{}_2$, —C(O)NR$^b{}_2$, —CF$_3$, —CN, and —NO$_2$; and wherein each R$^b$ is independently a C1-C5 branched or linear alkyl group.

20. The method of claim 18, wherein the subject expresses ΔF508 Cystic Fibrosis Transmembrane Conductance Regulator protein.

21. The method of claim 19, wherein X1 and X2 are —C(O)—.

22. The method of claim 21, wherein the compound is represented by structural formula III:

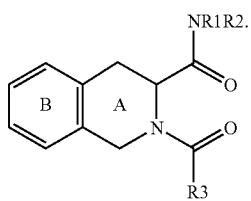

23. The method of claim 22, wherein

R1 is —H;

R2 is —X7-R6, wherein

X7 is a covalent bond or a C1-C12 alkyl chain optionally interrupted by —O— or —S—;

R6 is —SH, diphenylmethylene, or a 5 or 6 membered aryl, heteroaryl, heterocyclic or monocyclic C4-C6 cycloalkyl group;

each cyclic group represented by R6 is optionally substituted with one or more groups selected from C4-C6 cycloalkyl, halogen, —CF$_3$, —R$^d$, —OR$^d$, —SR$^d$, —COR$^d$, —OH, —SH, phenyl, phenoxyl, benzyl, benzoyl, N-morpholinyl, —NR$^d{}_2$, —NR$^d$COR$^e$, N-aniline, —NO$_2$, and —CN; and R3 is a six-membered aryl or heteroaryl group that is substituted or is fused to another ring.

24. The method of claim 23, wherein

R1 and R2 are independently —H or an optionally substituted aliphatic, aryl, heteroaryl, heterocyclic, or monocyclic cycloalkyl group, provided that R1 and R2 are not both —H;

or, R1 and R2, taken together with the nitrogen to which they are bonded, are an optionally substituted heterocyclic group; and R3 is an optionally substituted 2-naphthyl, 6-(1,4 benzodioxan)yl, 6-indolyl, or 2-(9-fluorenon)yl group, or a phenyl or pyridyl group substituted with one or more groups selected from halogen, —CF$_3$, —NO$_2$, —CN, —R$^c$, —OR$^c$, and —XR$^f$.

25. The method of claim 24, wherein the group represented by R$^f$ is optionally substituted with one or more groups selected from halogen, —CF$_3$, —NO$_2$, —CN, —R$^c$, and —OR$^c$.

26. The method of claim 25, wherein R3 is a substituted phenyl or pyridyl group.

27. The method of claim 26, wherein

R1 is H;

R2 is —X7-R6, wherein

X7 is a covalent bond or a C1-C4 alkyl chain optionally interrupted by —O— or —S—;

R6 is —SH, diphenylmethylene, or a phenyl, naphthyl, 3-quinolinyl, 6-quinolinyl, 2-thiazolyl, 2-furanyl, 5-indanyl, 2-(1,8-benzodiazin)yl, 6-( 1,4-benzodioxan)yl, 5-( 1,3-benzodioxol)yl, 5-benzimidazolyl, 3-pyridyl, or C4-C6 cycloalkyl group; and wherein the cyclic groups represented by R6 are optionally substituted with one or more groups selected from halogen, —CF$_3$, —R$^d$, —OR$^d$, —SR$^d$, —COR, —OH, —SH, phenyl, phenoxyl, benzyl, benzoyl, N-morpholine, —NR$^d{}_2$, —NR$^d$COR$^e$, N-aniline, —NO$_2$, —CN, and C4-C6 cycloalkyl.

28. The method of claim 22, wherein the compound is represented by structural formula IV:

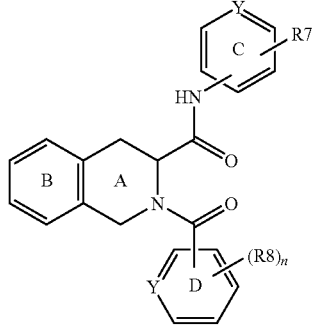

wherein
each Y is independently —N— or —CH—;
R7 is halogen, —CF$_3$, —R$^g$, —OR$^g$, —SR—$^g$, —COR, —OH, —SH, phenyl, phenoxyl, benzyl, benzoyl, N-morpholinyl, , —NR$^g_2$, —NR$^g$COR$^h$, N-aniline, —NO$_2$, —CN, or C4-C6 cycloalkyl;
each R8 is halogen, —CF$_3$, —NO$_2$, —CN, —R$^i$, —OR$^i$, or an optionally substituted phenoxy, phenyl sulfide, phenylsulfonyl, benzyl sulfide, benzyl, benzyloxy, benzoyl, —O-pyridyl, —CH$_2$-N-morpholine, —OCH$_2$CH$_2$-N-morpholine, cyclohexyloxy, or cyclopentyloxy group; and
n is 1 or 2; and
wherein R$^g$, R$^h$, and R$^i$ are each independently a C1-C8 branched or linear alkyl group.

29. The method of claim 28, wherein the compound is represented by structural formula V:

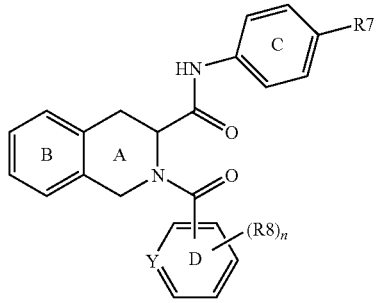

wherein
Y is —N— or —CH—;
R7 is —R$^j$, —NR$^j$(CO)R$^k$, or halogen;
each R8 is independently phenoxy, benzyloxy, C4-C6 cycloalkoxy, halogen, methoxy, ethoxy, 2-propyloxy, tert-butyloxy, 2-butyloxy, 3-pentyloxy, or methyl;
wherein R$^j$ is a C4-C8 linear alkyl group and R$^k$ is a C1-C4 branched or linear alkyl group.

30. A method of treating cystic fibrosis in a human in need of such treatment and carrying the homozygous ΔF508-CFTR mutation, comprising the step of administering to the subject an effective amount of a compound represented by structural formula VI administered to treat the subject for cystic fibrosis:

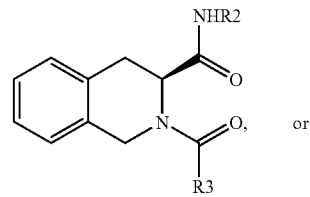

a pharmaceutically acceptable salt thereof, wherein
i) R3 is represented by structural formula R3$^a$:

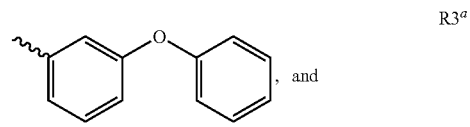

R2 is represented by one of structural formulas R2$^a$ to R2$^c$:

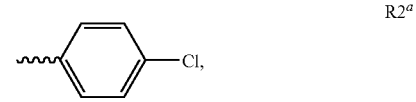

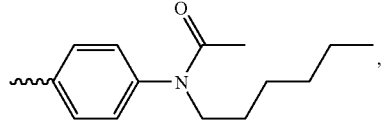

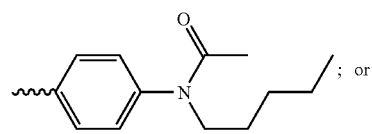

ii) R2 is represented by structural formula R2$^d$:

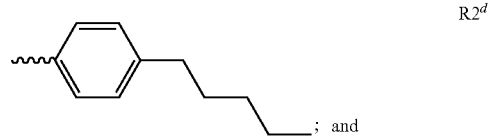

R3 is represented by one of structural formulas R3$^a$ or R3$^b$ to R3$^v$:

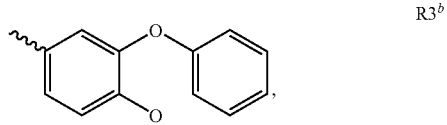

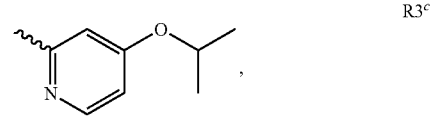

31. The method of claim 30, wherein R2 is represented by structural formula R2$^a$ and R3 is represented by structural formula R3$^a$.

32. The method of claim 30, wherein
R2 is represented by structural formula R2$^d$; and
R3 is represented by one of structural formulas R3$^a$ to R3$^g$.

33. The method of claim 30, wherein the subject expresses ΔF508 Cystic Fibrosis Transmembrane Conductance Regulator protein.

* * * * *